US012778814B2

(12) United States Patent
Schwartz et al.

(10) Patent No.: US 12,778,814 B2
(45) Date of Patent: Nov. 3, 2026

(54) APPARATUS AND METHOD FOR STRETCHING AND APPLYING ELASTIC SEGMENTS TO A CARRIER WEB

(71) Applicant: Curt G. Joa, Inc., Sheboygan Falls, WI (US)

(72) Inventors: Christopher A. Schwartz, Sheboygan Falls, WI (US); Andrew T. Coose, Sheboygan Falls, WI (US); Jeffrey W. Fritz, Sheboygan Falls, WI (US); Lloyd F. Kreif, Sheboygan Falls, WI (US)

(73) Assignee: CURT G. JOA, INC., Sheboygan Falls, WI (US)

(*) Notice: Subject to any disclaimer, the term of this patent is extended or adjusted under 35 U.S.C. 154(b) by 62 days.

(21) Appl. No.: 18/567,690

(22) PCT Filed: Jun. 8, 2022

(86) PCT No.: PCT/US2022/032735
§ 371 (c)(1),
(2) Date: Dec. 6, 2023

(87) PCT Pub. No.: WO2022/261254
PCT Pub. Date: Dec. 15, 2022

(65) Prior Publication Data

US 2024/0366434 A1 Nov. 7, 2024

Related U.S. Application Data

(60) Provisional application No. 63/202,380, filed on Jun. 9, 2021.

(51) Int. Cl.
*A61F 13/15* (2006.01)

(52) U.S. Cl.
CPC .. *A61F 13/15723* (2013.01); *A61F 13/15764* (2013.01); *A61F 2013/15926* (2013.01)

(58) Field of Classification Search
CPC ...... A61F 13/15764; A61F 2013/15926; A61F 13/15585; A61F 13/15593; A61F 13/15723
See application file for complete search history.

(56) References Cited

U.S. PATENT DOCUMENTS 3,833,973 A 9/1974 Schwarz
4,276,255 A 6/1981 Russell
(Continued)

FOREIGN PATENT DOCUMENTS

AU 199170140 A 8/1991
CA 2125807 A1 3/1994
(Continued)

OTHER PUBLICATIONS

International Search Report and Written Opinion issued in corresponding PCT Application No. US2022/032735, issued Sep. 14, 2022.

*Primary Examiner* — Daniel Jeremy Leeds
(74) *Attorney, Agent, or Firm* — Quarles & Brady LLP

(57) ABSTRACT

A method and apparatus for applying discrete stretched film portions to a carrier web includes conveying a continuous elastic film in a machine direction, operating a cutting unit to cut the continuous elastic film into a series of discrete first film portions and discrete second film portions, selectively adjusting a feed rate of the continuous elastic film upstream of the cutting unit, transferring a first film portion and a second film portion from a vacuum drum to a first pair of arms and a second pair of arms of, respectively, of a stretch unit, stretching the first and second film portions in a cross-machine direction by separating the first and second pairs of arms in the cross-machine direction as the stretch unit rotates from a pickup position to a transfer position, and
(Continued)

transferring the stretched first and second film portions from the stretch unit to the carrier web.

22 Claims, 14 Drawing Sheets

(56) References Cited

U.S. PATENT DOCUMENTS

| | | | |
|---|---|---|---|
| 4,925,520 | A * | 5/1990 | Beaudoin .......... A61F 13/15601 156/519 |
| 5,000,806 | A | 3/1991 | Merkatoris et al. |
| 5,043,036 | A | 8/1991 | Swenson |
| 5,102,486 | A | 4/1992 | Midgley et al. |
| 5,308,345 | A | 5/1994 | Herrin |
| 6,648,122 | B1 | 11/2003 | Hirsch et al. |
| 6,763,749 | B2 | 7/2004 | Droste et al. |
| 6,957,160 | B2 | 10/2005 | Miller et al. |
| 7,172,666 | B2 | 2/2007 | Groves et al. |
| 7,347,914 | B2 | 3/2008 | Umebayashi et al. |
| 9,809,414 | B2 * | 11/2017 | Fritz ................. A61F 13/15804 |
| 11,737,930 | B2 * | 8/2023 | Kreif .................... B65H 29/241 156/265 |
| 2005/0145322 | A1 | 7/2005 | Hoffman et al. |
| 2008/0093015 | A1 | 4/2008 | Chang et al. |
| 2009/0294044 | A1 | 12/2009 | Gill et al. |
| 2009/0306617 | A1 | 12/2009 | Tsang et al. |
| 2010/0175807 | A1 | 7/2010 | Yamamoto |
| 2013/0035222 | A1 | 2/2013 | Andrews et al. |
| 2013/0178349 | A1 | 7/2013 | Yanashima et al. |
| 2014/0041786 | A1 | 2/2014 | Henke et al. |
| 2018/0042779 | A1 * | 2/2018 | Lenser .............. A61F 13/49019 |
| 2018/0042780 | A1 | 2/2018 | Lenser et al. |
| 2018/0170026 | A1 | 6/2018 | Schneider et al. |
| 2020/0170846 | A1 | 6/2020 | Lenser et al. |
| 2020/0179179 | A1 | 6/2020 | Lenser et al. |
| 2020/0268563 | A1 | 8/2020 | Lenser et al. |
| 2020/0375807 | A1 | 12/2020 | Schneider et al. |
| 2021/0085532 | A1 | 3/2021 | Lenser et al. |
| 2021/0128366 | A1 | 5/2021 | Schneider et al. |
| 2021/0186770 | A1 | 6/2021 | Lenser et al. |
| 2021/0307970 | A1 | 10/2021 | Lenser et al. |
| 2022/0233362 | A1 | 7/2022 | Lenser et al. |
| 2022/0257427 | A1 | 8/2022 | Schneider et al. |
| 2022/0287887 | A1 | 9/2022 | Lenser et al. |
| 2023/0157900 | A1 | 5/2023 | Lenser et al. |
| 2023/0248581 | A1 | 8/2023 | Lenser et al. |

FOREIGN PATENT DOCUMENTS

| | | | |
|---|---|---|---|
| CA | 2559517 | A1 | 4/2007 |
| CN | 106137544 | A | 11/2016 |
| DE | 19520513 | C1 | 7/1996 |
| EP | 338662 | A2 | 10/1989 |
| EP | 741999 | A1 | 11/1996 |
| EP | 1440026 | B1 | 6/2006 |
| EP | 3028687 | A1 | 6/2016 |
| EP | 3278779 | A1 | 2/2018 |
| EP | 3278780 | A1 | 2/2018 |
| EP | 3415131 | A1 | 12/2018 |
| FI | 200605201 | A | 9/2007 |
| JP | 2008140 | A | 1/1990 |
| JP | 11140706 | A | 5/1999 |
| JP | 2014014450 | A | 1/2014 |
| JP | 2021133515 | A | 9/2021 |
| JP | 2021134045 | A | 9/2021 |
| WO | 1995033618 | A1 | 12/1995 |
| WO | 2007133128 | A1 | 11/2007 |
| WO | 2010046738 | A1 | 4/2010 |
| WO | 2010078572 | A1 | 7/2010 |
| WO | 2010136909 | A1 | 12/2010 |
| WO | 2013172957 | A1 | 11/2013 |
| WO | 2014182777 | A1 | 11/2014 |
| WO | 2015042351 | A1 | 3/2015 |
| WO | 2015168032 | A1 | 11/2015 |
| WO | 2018031839 | A1 | 2/2018 |
| WO | 2020121094 | A1 | 6/2020 |
| WO | 2021263066 | A1 | 12/2021 |

* cited by examiner

APPARATUS AND METHOD FOR STRETCHING AND APPLYING ELASTIC SEGMENTS TO A CARRIER WEB

CROSS REFERENCE TO RELATED APPLICATION

This application is the U.S. National Stage of PCT/US2022/032735 with international filing date of Jun. 8, 2022, and which claims priority to U.S. Provisional Application No. 63/202,380 filed on Jun. 9, 2021, the contents of which are incorporated by reference in their entireties.

BACKGROUND OF THE INVENTION

Embodiments of the invention relate to a method and apparatus for stretching and applying elastic segments to a carrier web in the manufacture of disposable absorbent articles such as diapers or incontinence control garments. More particularly, embodiments of the invention relate to such a method and apparatus enable the pitch or spacing between adjacent stretched elastic segments applied onto the carrier web to be varied. By selectively controlling the feed rate at which a continuous elastic film is fed in the machine direction for cutting, stretching, and application of elastic segments formed therefrom, the spacing between the elastic segments can be varied in a desired manner.

Disposable absorbent articles, such as diapers of the children's training pant-type or of the adult incontinence type, are typically formed from a combination of multiple web layers, absorbent structures, and elastic elements. The articles may thus include a thin flexible liquid impermeable backing sheet on which a permeable nonwoven sheet is overlayed. An absorbent pad is disposed between the two sheets and the sheets are adhered at their edges to form a unitary article that prevents liquid body exudates from seeping out of the edges of the diaper. Elastic elements, such as an elastic waist element and elastic leg cuffs, are provided in the article to help the article better conform to the body of the wearer around the waist, back, and legs so as to prevent leakage along the interface of the nonwoven sheet which is in contact with the body.

In the manufacture of absorbent articles as described above, the elastic elements are often provided in the form of an arrangement of elastic strands that are sandwiched between a topsheet and a back sheet and captured in adhesive to secure them in place. The elastic strands may be applied along the waistline of an article on at least one of the front side and the back side thereof and/or along both sides of the crotch of the article to form a barrier along the sides of an absorbent core.

Examples of articles that include such an arrangement of elastic strands are provided in FIGS. 1A and 1B. In FIG. 1A, the article 2 is provided in the form of a light incontinence absorbent article, while in FIG. 1B the article 2 is provided in the form of a pants-type article, with it being recognized that other product configurations such as baby diapers, for example, could also include such elastic strands. As shown in each of the embodiments of FIGS. 1A and 1B, the article 2 includes a plurality of discrete elastic strands 4 positioned along either side of a crotch region that includes an absorbent core 6. The elastic strands 4 may be applied in a stretched condition and secured between a topsheet and bottom sheet (collectively indicated at 8) of the article 2 via use of an adhesive.

While articles that incorporate arrangements of elastic strands for forming an elastic waistband and/or elastic leg cuffs are generally effective in preventing liquid body exudates from seeping out of the edges of the article, the disposable hygiene industry experiences a constantly evolving series of product designs and material innovations that existing manufacturing processes and associated system machinery may be unable to accommodate.

It is therefore desirable to provide improved methods and apparatuses for forming and applying elastic materials to disposable absorbent articles.

BRIEF DESCRIPTION OF THE INVENTION

In accordance with one aspect of the invention, a method of applying discrete stretched film portions to a carrier web includes conveying a continuous elastic film in a machine direction (MD), operating a cutting unit to cut the continuous elastic film into a series of discrete first film portions and discrete second film portions, selectively adjusting a feed rate of the continuous elastic film upstream of the cutting unit, transferring a first film portion of the series of discrete first film portions from a vacuum drum to a first pair of arms of a stretch unit, and transferring a second film portion of the series of discrete second film portions from the vacuum drum to a second pair of arms of the stretch unit. The method also includes stretching the first film portion in a cross-machine direction (CD) by separating the first pair of arms in the CD as the stretch unit rotates from a pickup position to a transfer position, stretching the second film portion in the CD by separating the second pair of arms in the CD as the stretch unit rotates from the pickup position to the transfer position, and transferring the stretched first and second film portions from the stretch unit to the carrier web.

A drive roll may be operated to feed the continuous elastic film onto the vacuum drum at a first feed rate, cutting the continuous elastic film with the cutting unit while the continuous elastic film is being fed at the first feed rate, to form a first film portion pair including the first film portion and the second film portion; and subsequent to forming the first film portion pair, operating the drive roll to feed the continuous elastic film onto the vacuum drum at a second feed rate that is lower than the first feed rate. The drive roll also may be operated to feed the continuous elastic film onto the vacuum drum at the second feed rate for a pre-determined time period or for a pre-determined length of the continuous elastic film, operating the drive roll to feed the continuous elastic film onto the vacuum drum at the first feed rate after the pre-determined time period has passed or after the pre-determined length of the continuous elastic film has been fed. and cutting the continuous elastic film with the cutting unit while the continuous elastic film is being fed at the first feed rate, to form a second film portion pair including another first film portion of the series of discrete first film portions and another second film portion of the series of discrete second film portions.

The another first film portion may be transferred from the vacuum drum to a third pair of arms of the stretch unit, transferring the another second film portion from the vacuum drum to a fourth pair of arms of the stretch unit, stretching the another first film portion in the CD by separating the third pair of arms in the CD as the stretch unit rotates from the pickup position to the transfer position, and stretching the another second film portion in the CD by separating the fourth pair of arms in the CD as the stretch unit rotates from the pickup position to the transfer position, and transferring the stretched another first and second film portions from the stretch unit to the carrier web.

In transferring the stretched first and second film portions and in transferring the stretched another first and second film portions, the stretched first and second film portions of the first film portion pair may be spaced apart on the carrier web in the MD by a first distance and the stretched another first and second film portions of the second film portion pair may be spaced apart on the carrier web in the MD by the first distance. The first film portion pair on the carrier web apart from the second film portion pair in the MD may also be spaced by a second distance greater than the first distance.

In the method as disclosed herein, transferring the first and second film portions and transferring the another first and second first film portions from the vacuum drum may include rotating the stretch unit to position the first pair of arms and the second pair of arms adjacent the vacuum drum to remove the first and second film portions from the vacuum drum, and rotating the stretch unit to position the third pair of arms and the fourth pair of arms adjacent the vacuum drum to remove the another first and second film portions from the vacuum drum.

In some embodiments the stretch unit is rotated at a constant speed.

Rotational power may be provided to the drive roll via a servo motor to selectively cause the drive roll to feed the continuous elastic film onto the vacuum drum at the first feed rate or the second feed rate.

In some embodiments, the cutting unit comprises a rotating cutting wheel having a first cutting element and a second cutting element fixedly positioned thereon so as to be proximate each other on the rotating cutting wheel, and operating the cutting unit includes performing a pair of cuts with the first and second cutting elements to form the first film portion and the second film portion, rotating the rotating cutting wheel a full revolution, and performing another pair of cuts with the first and second cutting elements to form the another first film portion and the another second film portion.

Some embodiments of the disclosed method include rotating the vacuum drum at a drum speed that is higher than the first feed rate and the second feed rate at which the continuous elastic film is fed onto the vacuum drum, such that a leading edge of the continuous elastic film slips over a surface of the vacuum drum as it is fed onto the vacuum drum.

In accordance with another aspect of the invention, an apparatus for applying stretched elastic segments to a carrier web includes a drive roll configured to feed a continuous elastic film in a machine direction (MD), a vacuum drum positioned to receive the continuous elastic film from the drive roll, and a cutting unit positioned adjacent the vacuum drum and configured to cut the continuous elastic film to create a series of discrete first film portions and discrete second film portions. The apparatus also includes a stretch unit to transfer the series of discrete first film portions and discrete second film portions from a pickup position off the vacuum drum to a transfer position onto the carrier web, with the stretch unit further including a first pair of arms configured to transfer a first film portion of the series of discrete first film portions from the vacuum drum, the first pair of arms being separable in a cross-machine direction (CD) and a second pair of arms configured to transfer a second film portion of the series of discrete second film portions from the vacuum drum, the second pair of arms being separable in the CD, wherein each of the first pair of arms and the second pair of arms separate outwardly in the CD as they move from the pickup position to the transfer position, to stretch the first film portion and the second film portion, respectively, in the CD. The drive roll is operable to variably feed the continuous elastic film onto the vacuum drum at a first feed rate and a second feed rate that is slower than the first feed rate.

A servo motor may be configured to selectively drive the drive roll to feed the continuous elastic film onto the vacuum drum at one of the first feed rate and the second feed rate, with a controller operably connected to the servo motor to control operation of the servo motor.

The controller may be configured to operate the servo motor to cause the drive roll to feed the continuous elastic film onto the vacuum drum at the first feed rate for either a first pre-determined period of time or a first pre-determined length of the continuous elastic film, and operate the servo motor to cause the drive roll to feed the continuous elastic film onto the vacuum drum at the second feed rate for either a second pre-determined period of time or a second pre-determined length of the continuous elastic film. The servo motor may be operated to cause the drive roll to alternately feed the continuous elastic film onto the vacuum drum at the first and second feed rates during ongoing operation.

In some embodiments, the cutting unit includes a rotating cutting wheel and a first cutting element and a second cutting element affixed to the rotating cutting wheel. The first cutting element and the second cutting element are positioned proximate each other on one side of the rotating cutting wheel.

The controller may be configured to coordinate rotation of the rotating cutting wheel with operation of the servo motor, such that the first and second cutting elements are positioned to cut the continuous elastic film during or just prior to a transition of the feed rate from the first feed rate to the second feed rate and such that the first and second cutting elements rotate through a non-cutting range while the feed rate is at the second feed rate.

The stretch unit may include a third pair of arms configured to pick-up another first film portion of the series of discrete first film portions from the vacuum drum, the third pair of arms being separable in the CD machine and a fourth pair of arms configured to pick-up another second film portion of the series of discrete second film portions from the vacuum drum, the fourth pair of arms being separable in the CD machine, wherein each of the third pair of arms and the fourth pair of arms separate outwardly in the CD direction as they move from the pickup position to the transfer position, such that the another first film portion and the another second film portion, respectively, are stretched in the CD direction.

In accordance with yet another aspect of the invention, a method of applying discrete stretched film portions to a carrier web includes operating a drive roll to feed a continuous elastic film in a machine direction (MD) onto a vacuum drum and operating a cutting unit to form a series of discrete first film portions and discrete second film portions from the continuous elastic film. The method also includes operating a stretch unit comprising a plurality of pairs of arms to rotatably transfer the series of discrete first film portions and discrete second film portions from a pickup position off the vacuum drum to a transfer position onto the carrier web, with each pair of arms of the plurality of pairs of arms securing a respective first film portion or second film portion thereto, stretch each respective first film portion and second film portion in a cross-machine direction (CD) by separating each pair of arms of the plurality of pairs of arms in the CD between the pickup position and the transfer position, and deposit the series of discrete first film portions and discrete second film portions onto the carrier web at the transfer position. A first film portion and a second film portion of a first film portion pair deposited on the carrier web are separated in the MD by a first distance and a second film portion pair, including an another first film portion and an another second film portion, deposited on the carrier web is separated in the MD from the first film portion pair by a second distance greater than the first distance.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings.

DETAILED DESCRIPTION

Embodiments of the invention are directed to an apparatus for applying stretched elastic segments to a carrier web and method of operating thereof. Although the disclosure hereof is provided in sufficient detail to enable those skilled in the art to practice the invention, the physical embodiments herein disclosed merely exemplify the invention, which may be embodied in other specific structures. While the preferred embodiment has been described, the details may be changed without departing from the invention.

Embodiments of the invention enable stretched elastic material strips to be used in the manufacture of disposable absorbent articles in place of the typical elastic strands. These elastic material strips may be used to create elasticized leg regions for leg elastic or leg cuffs (right and left leg cuffs), i.e., “soft cuffs,” instead of an arrangement of discrete elastic strands for improved user comfort and/or appearance. The formation of elastic strip leg cuffs, and subsequent application thereof onto a carrier web, may require that the pitch between elastic strip leg cuffs be varied, and existing manufacturing processes and associated system machinery are at present unable to accommodate such variations in pitch. The improved method and apparatus disclosed herein allows the pitch between adjacent elastic material portions to be varied to, for example, enable the formation and application of left and right elastic leg cuffs for an absorbent article using only a single cutting unit and stretch unit.

Figure 1B:
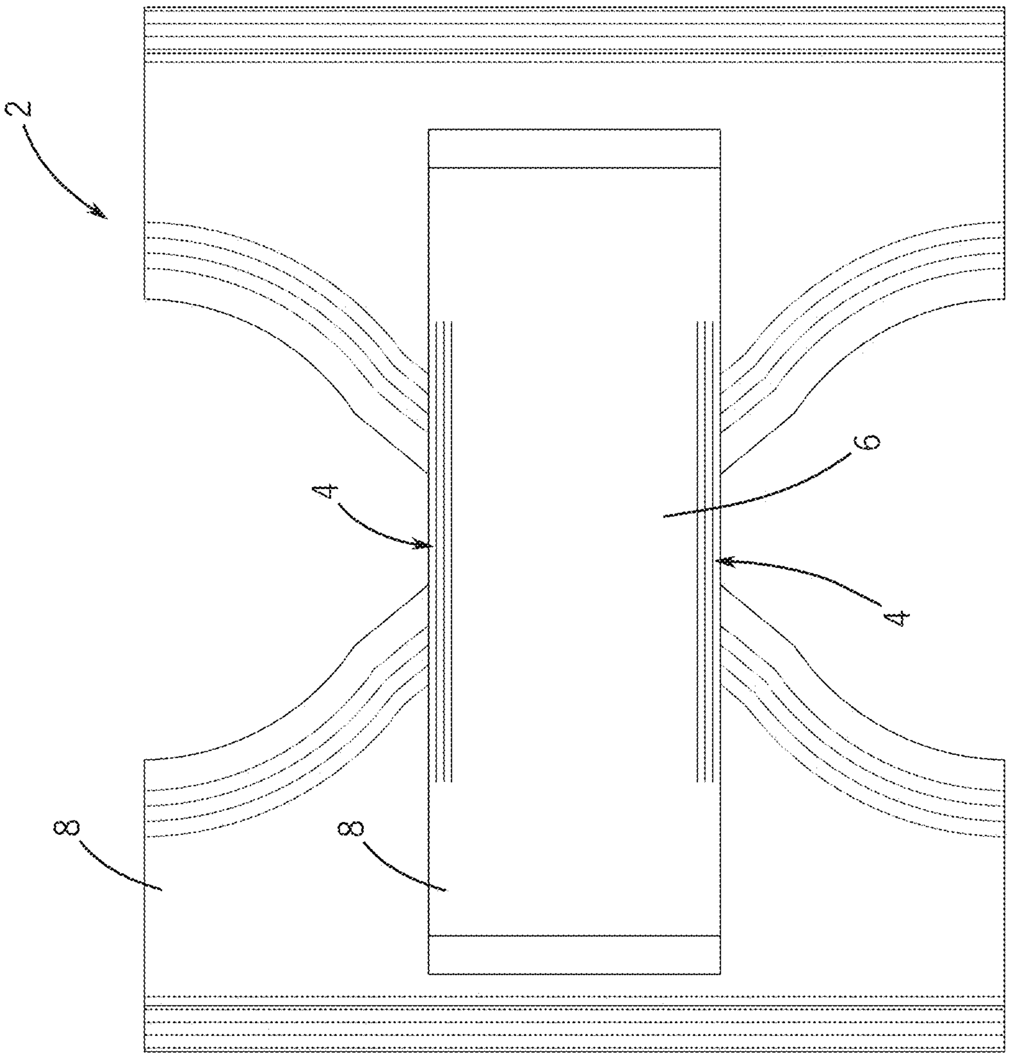
FIG. 1B PRIOR ART
FIGS. 1A and 1B depict typical absorbent articles that include an arrangement of elastic strands, as known in the prior art.
Figure 1A:
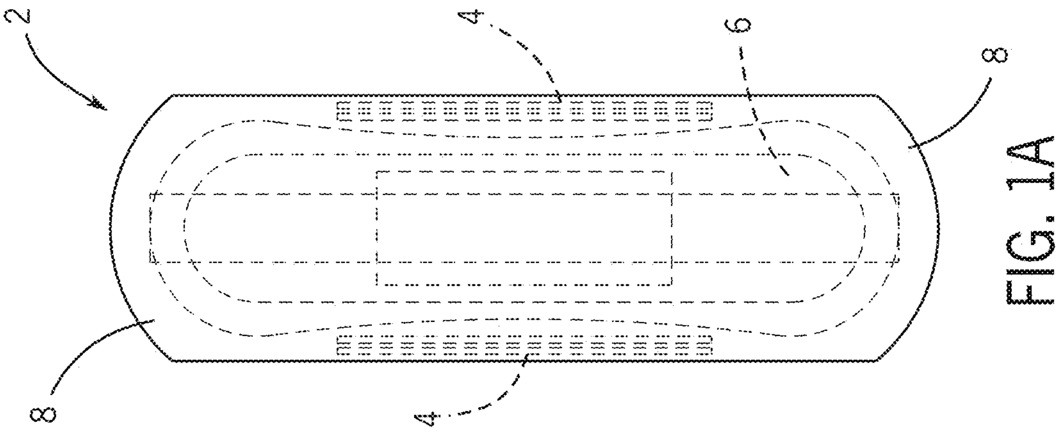
FIG. 1A PRIOR ART
Figure 2B:
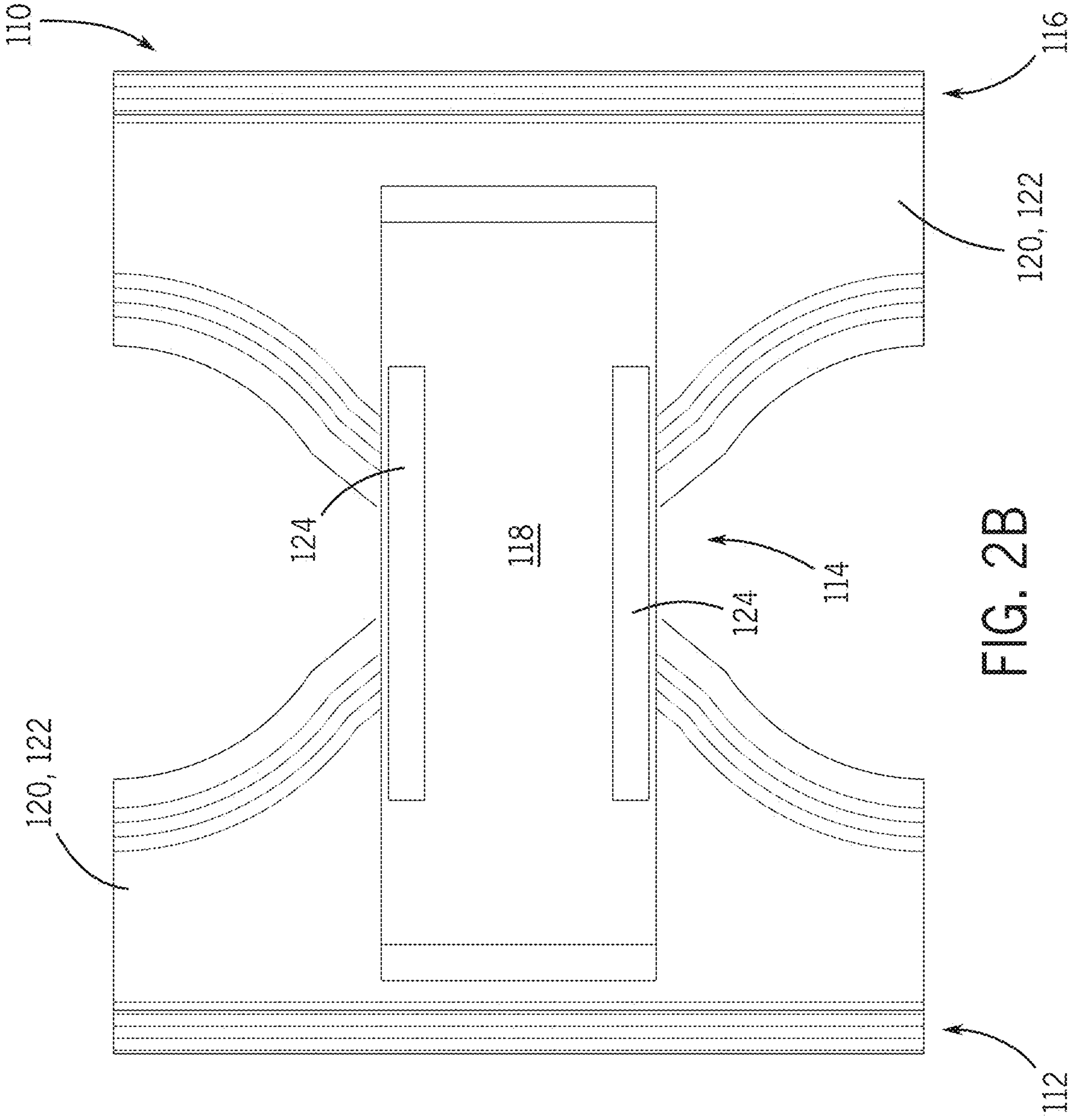
FIG. 2B depicts a pants-type absorbent article that includes elastic elements that may be formed and applied via a method and apparatus of the invention.
Figure 2A:
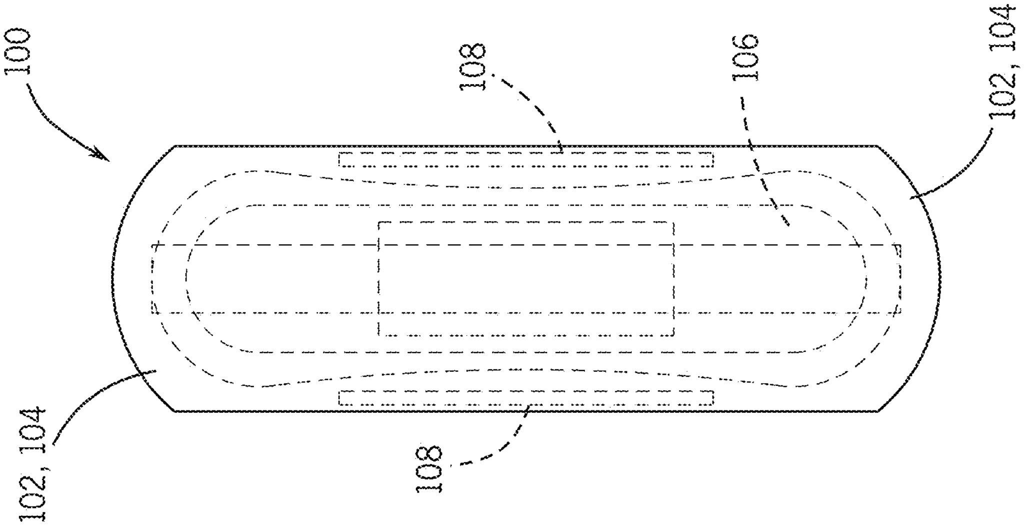
FIG. 2A depicts a light incontinence absorbent article that includes elastic elements that may be formed and applied via a method and apparatus of the invention.

Referring now to FIG. 2A, a plan view of an example absorbent article 100 is provided that may be produced (in part) via use of a method and apparatus for stretching and applying elastic segments to a carrier web, as described here after. The absorbent article 100 illustrated in FIG. 2A represents a light incontinence article or pad. The light incontinence article 100 generally comprises a combination of multiple web layers, absorbent structures, and elastic elements that are joined and bonded together. In particular, the article may include a topsheet 102, a back sheet 104, an absorbent core 106, and a pair of elasticized cuffs 108.

The topsheet 102 is provided as a liquid-permeable topsheet that constitutes a skin-facing side of the disposable article 100 and thus comes into contact with the wearer. The topsheet 102 has fibers and may be formed of a non-woven fabric. The back sheet 104 is provided on a non-skin-facing side of the disposable article 100 opposite the topsheet 102. The back sheet 104 has fibers and may be formed of a non-woven fabric.

The absorbent core 106 lies across the crotch region of a wearer and is capable of absorbing and retaining liquid body exudates. The size and the absorbent capacity of the absorbent core 106 may vary based on the size of the intended wearer and the liquid loading imparted by the intended use of the absorbent article. The absorbent core 106 may be manufactured in a variety of shapes and from a variety of materials, including cellulosic fluff pulp, tissue layers, highly absorbent polymers (so called superabsorbent polymer particles (SAP)), absorbent foam materials, absorbent nonwoven materials, or the like.

The elasticized cuffs 108 are joined onto the topsheet 102 and disposed at least in part along widthwise outer sides of the disposable article 100. The cuffs 108 are aligned substantially symmetrically with respect to an axis of symmetry extending along the widthwise center of the disposable article 100. The cuffs 108 may be formed from strips of elastic material that are joined to the topsheet 102, such as via an adhesive, and are either positioned on a skin-facing surface of the topsheet 102 or between the topsheet 102 and the back sheet 104. The elasticized cuffs 108 form walls rising toward the skin-facing side along outer edges of the absorbent core 106 to prevent exudate from leaking sideward.

Another example absorbent article 110 that may be produced (in part) via use of a method and apparatus for stretching and applying elastic segments to a carrier web is shown in FIG. 2B. The absorbent article 110 illustrated in FIG. 2B represents a “pants-type” article such as a children’s training pant-type or of the adult incontinence type pant garment. The pants-type article 110 generally comprises a combination of multiple web layers, absorbent structures, and elastic elements that are joined and bonded together to form waist and leg openings, similar to shorts or the like. The article 110 includes a front waistline region 112, a crotch region 114, and a rear waistline region 116. The front waistline region 112 is a portion coming into contact with a front waistline region (belly portion) of a wearer. The rear waistline region 116 is a portion coming into contact with the rear waistline region (back portion) of the wearer. The crotch region 114 is located between the front waistline region 102 and the rear waistline region 116.

The article 100 includes an absorbent core 118 that lies across the crotch region 114 and extends toward at least one of the front waistline region 112 and the rear waistline region 116. The illustrated absorbent core 118 is disposed across the front waistline region 112, the crotch region 114, and the rear waistline region 116, and is capable of absorbing and retaining liquid body exudates.

A liquid-permeable topsheet 120 is provided and constitutes a skin-facing side of the disposable article 110 and thus comes into contact with the wearer. The topsheet 120 is disposed across the front waistline region 112, the crotch region 114, and the rear waistline region 116. A back sheet 122 is provided on a non-skin-facing side of the disposable article 110 opposite the topsheet 120 and is also generally disposed across the front waistline region 112, the crotch region 114, and the rear waistline region 116.

A pair of elasticized cuffs 124 are joined onto the topsheet 120 and disposed at least in part along widthwise outer sides of the disposable article 110 to form walls rising toward the skin-facing side along outer edges of the absorbent core 108 to prevent exudate from leaking sideward. The cuffs 124 are aligned substantially symmetrically with respect to an axis of symmetry extending along the widthwise center of the disposable article 110. The cuffs 124 may be formed from strips of elastic material that are joined to the topsheet 120, such as via an adhesive, and are either positioned on a skin-facing surface of the topsheet 120 or between the topsheet 120 and the back sheet 122.

Figure 3:
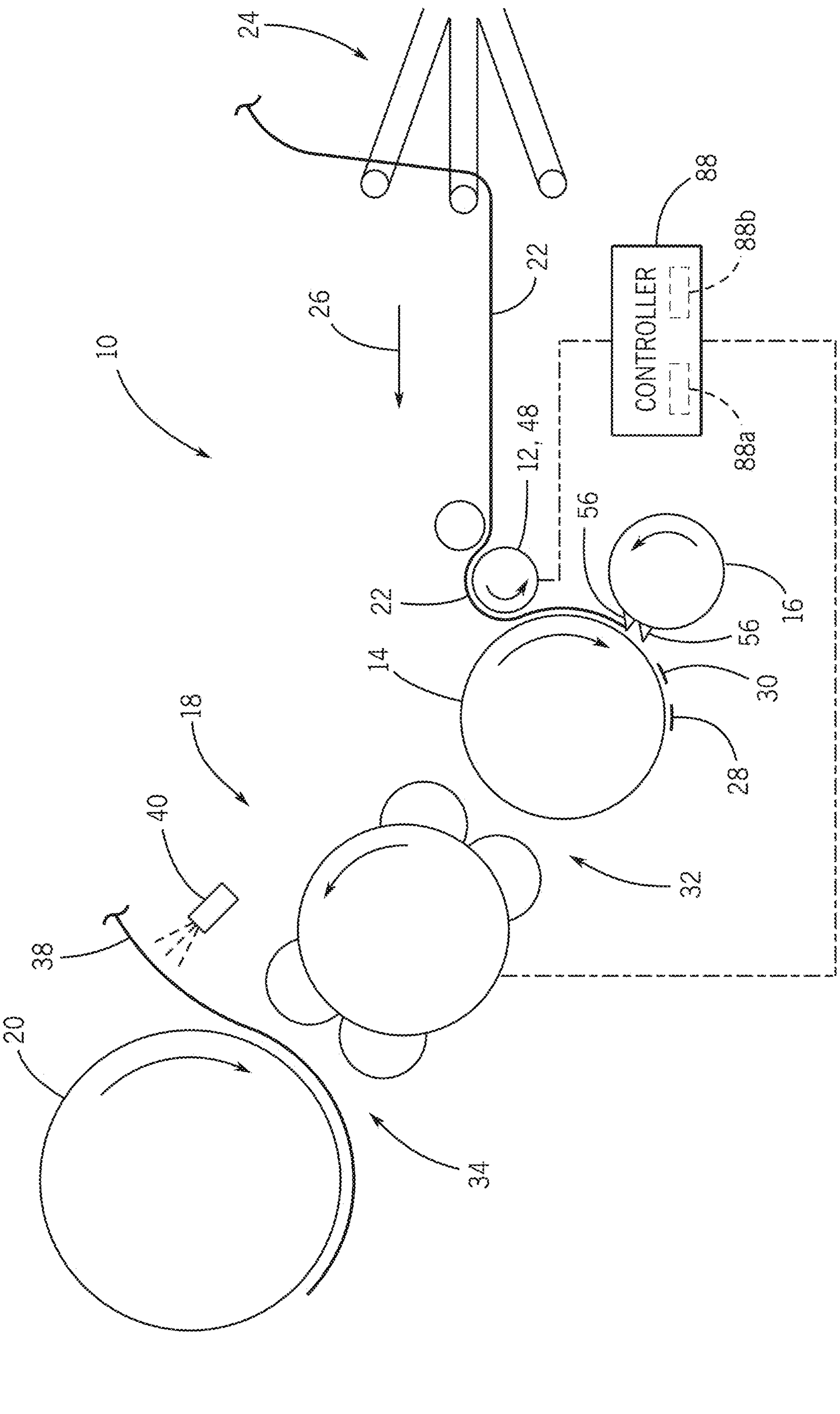
FIG. 3 is a schematic view illustrating the layout of an apparatus for forming, stretching, and applying elastic segments to a carrier web, according to an embodiment of the invention.

Referring now to FIG. 3, a schematic diagram of an example apparatus 10 is illustrated that, in one implementation, may form the strips of elastic material that make up the cuffs 108, 124 of the articles 100, 110 shown in FIGS. 2A and 2B, and that then stretches and applies the elastic strips to a moving carrier web (e.g., the topsheet 102, 120) as part of the process of manufacturing the article 100, 110. The principal components of the apparatus 10 include a drive roll 12, a vacuum roll or drum 14, a cutting unit 16, an elastic stretch unit 18, and a transfer drum 20, although it is recognized that additional components may be included in the apparatus 10 that enable a desired operation thereof, including various actuators, sensors, material feeds and the like.

In operation of the apparatus 10, a continuous elastic film 22 formed of elastic polyurethane foam material, for example, is fed into the apparatus 10, such as by an arrangement of rolls (not shown) that draw in the elastic film 22 from a material roll and provide the elastic film 22 to the apparatus 10 for subsequent processing. The elastic film 22 is fed over a dancer roll arrangement 24 that senses a tension of the elastic film 22 between that arrangement of rolls and the drive roll 12 and operates to maintain a constant tension on the elastic film 22. The drive roll 12 then feeds the elastic film 22 onto the vacuum drum 14, with the elastic film 22 moving in a machine direction (generally indicated by 26). The cutting unit 16 acts on the elastic film 22 to form a series of discrete film portions that can be characterized as discrete first film portions 28 and discrete second film portions 30 that, for example, will form the left and right elasticized cuffs of an absorbent article. The discrete film portions 28, 30 are maintained on the vacuum drum 14 as it rotates about its axis of rotation, until the film portions 28, 30 are positioned at a pickup location 32. At the pickup location 32, the stretch unit 18 operates to remove the film portions 28, 30 from the vacuum drum 14, with the film portions 28, 30 being retained on the stretch unit 18 as the stretch unit rotates. The stretch unit 18 retains the film portions 28, 30 thereon as it rotates from the pickup location 32 to a transfer location 34, with the stretch unit 18 operating to stretch the film portions 28, 30 in a cross-machine direction (generally indicated by 36, FIG. 4) as it moves from the pickup location 32 to the transfer location 34, as will be explained in greater detail below.

When the stretched film portions 28, 30 arrive at the transfer location 34, the stretched film portions 28, 30 are transferred from the stretch unit 18 onto a carrier web 38 that is moving in the machine direction 26. An adhesive applicator 40 may be positioned over the incoming carrier web 38 and arranged such that a row of nozzles or other application devices extend transversely (in the cross-machine direction 36) across carrier web 38. The applicator 40 may lay down stripes of adhesive in a desired intermittent pattern at locations that the elastic film portions 28, 30 are to be placed onto the carrier web 38. The transfer drum 20, which is positioned on an opposite side of the carrier web 38 (i.e., opposite from the stretch unit 18), facilitates the transfer of the stretched film portions 28, 30 onto the carrier web 38, with the carrier web 38 passing between the transfer drum 20 and the stretch unit 18 at the transfer location 34 to receive the stretched elastic portions 28, 30 from the stretch unit 18 at the locations at which adhesive has been applied. The carrier web 38, with the stretched film portions 28, 30 retained thereon, may then continue downstream in the machine direction 26 for further processing in order to complete the assembly of the absorbent article.

Figure 4:
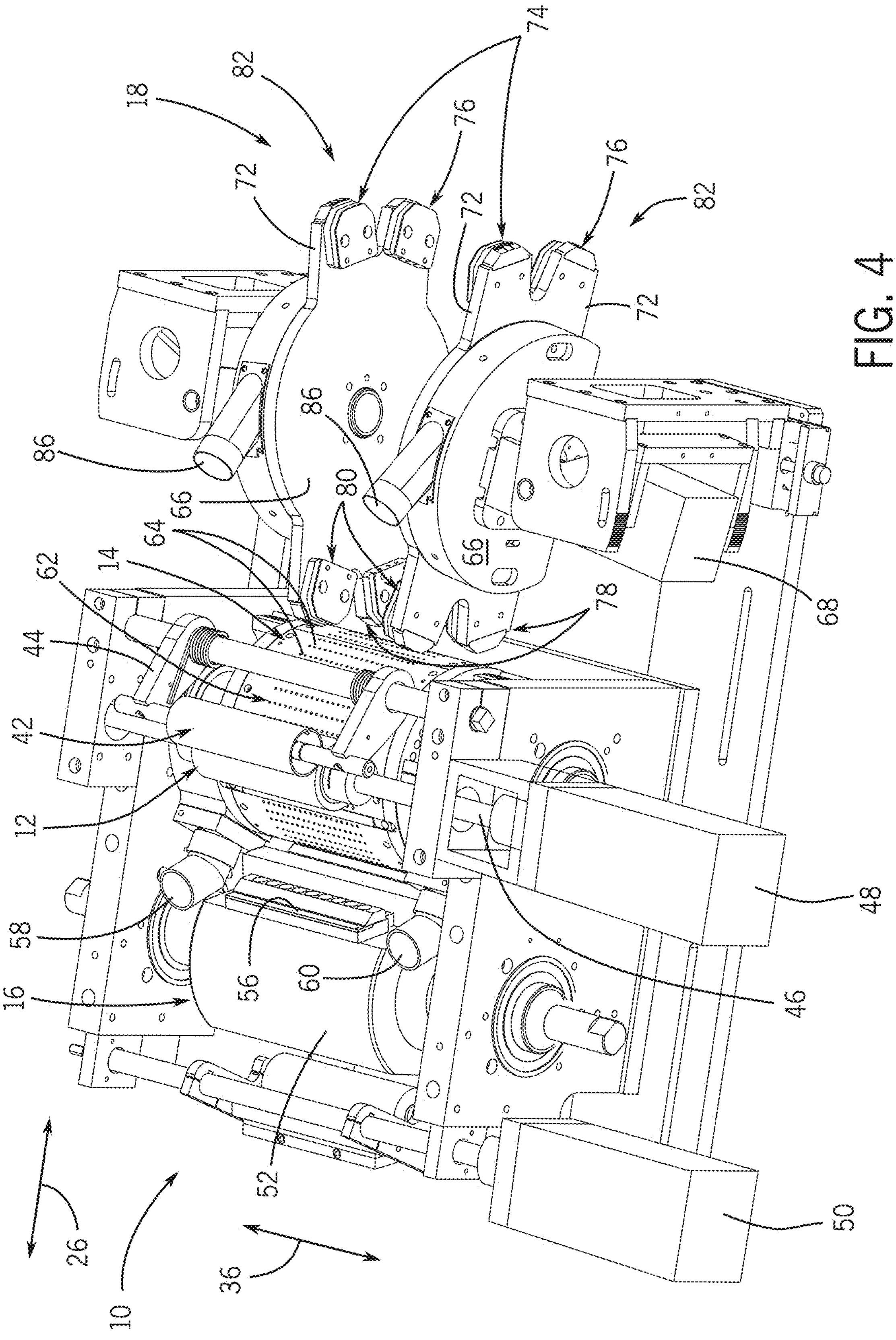
FIG. 4 is a front perspective view of a portion of the apparatus of FIG. 3.

Referring now to FIG. 4, and with continued reference to FIG. 3, a perspective view of a portion of the apparatus 10 is provided to further illustrate individual components thereof. As previously indicated, a continuous elastic film 22 is fed into the apparatus 10 and, specifically, to the drive roll 12 thereof. The continuous elastic film 22 is received on the drive roll 12 and retained thereon via an adjacent support roll 42 positioned on a spring biased arm 44 that pinches the film against drive roll 12. The drive roll 12 is supported on a drive shaft 46 that receives rotational power from a rotating actuator 48 that, in one embodiment, may be provided as a servo motor (referred to hereafter as "servo motor 48"). Through a servo camming configuration/process, the servo motor 48 controls a rotational speed of the drive roll 12 to thereby also control a feed rate at which the drive roll 12 provides the continuous elastic film 22 to the vacuum drum 14, as will be explained in greater detail here after. In alternative embodiments, other types of rotating actuators may be used instead of a servo motor, such as a stepper motor or other electric motor that be selectively operated to control a rotational speed of the drive roll 12 to thereby also control a feed rate at which the drive roll 12 provides the continuous elastic film 22 to the vacuum drum 14.

The vacuum drum 14 is positioned to receive the continuous elastic film 22 from the drive roll 12 after passing therethrough, with the cutting unit 16 positioned adjacent to the vacuum drum 14 to perform a cutting operation on the continuous elastic film 22 and thereby form discrete elastic film portions 28, 30. The vacuum drum 14 and cutting unit 16 may be driven via a common servo motor 50, with the servo motor 50 providing a rotational power to a cutting wheel 52 of the cutting unit 16 and to the vacuum drum 14 via a timing belt (not shown) extending between the servo motor 50 and the cutting unit 16 and vacuum drum 14. In one embodiment, both the vacuum drum 14 and cutting unit 16 are rotated at a constant speed.

The cutting unit 16 rotates about an axis such that a pair of cutting knives 56 mounted on the cutting wheel 52 are positioned to periodically come in contact with the continuous elastic film 22. The cutting knives 56 rotate into contact with the periphery of vacuum drum 14 and use the drum as an anvil for cutting individual film portions 28, 30 from the continuous elastic film 22. The pair of cutting knives 56 are positioned proximate each other such that they cut the continuous elastic film 22 in quick succession, performing two cuts on the elastic film 22 and creating a pair of elastic film portions—i.e., the first film portion 28 and the second film portion 30. As one non-limiting example, the cutting knives 56 may be positioned on the cutting wheel 52 and rotate thereabout at a speed that provides for a cutting of the continuous elastic film 22 to form film portions 28, 30 having a length in the machine direction 26 of between 20-80 mm. After completing the pair of cuts, the cutting knives 56 continue to rotate about the axis and make a full revolution before again being brought into a cutting position. It is contemplated that cutting unit 16 may be provided with only a single cutting knife or three or more cutting knives in alternative embodiments. In such instances, the rotational speed of the cutting unit 16 may be selectively varied so as to cut the continuous elastic film 22 and form film portions 28,30 in the desired length.

The discrete film portions 28, 30 cut from the continuous elastic film 22 are secured to the vacuum drum 14 after the cuts performed by the cutting unit 16. Vacuum pipes 58, 60 are provided that draw a vacuum into an interior vacuum chamber (not shown) of the vacuum drum 14. In one embodiment, pipe 58 draws a low vacuum into the vacuum chamber to draw the continuous elastic film 22 onto the vacuum drum 14 prior to being cut (while allowing for a slipping of the film 22 on the drum 14) and pipe 60 draws a higher vacuum into the vacuum chamber to hold the cut-off film portions 28, 30 in a fixed position on drum 20. As can be seen in FIG. 4, an outer surface 62 of the vacuum drum 14 includes a plurality of holes or slots 64 in fluid communication with the interior vacuum chamber and through which vacuum is drawn. The vacuum drum 14 is thus configured to hold the elastic film portions 28, 30 to the periphery of the vacuum drum 14 as the vacuum drum rotates from the location where the film portions 28, 30 are cut from the continuous film to the location where the film portions 28, 30 will be picked off of the vacuum drum 14 by the stretch unit 18, i.e., pickup location 32.

Figure 5:
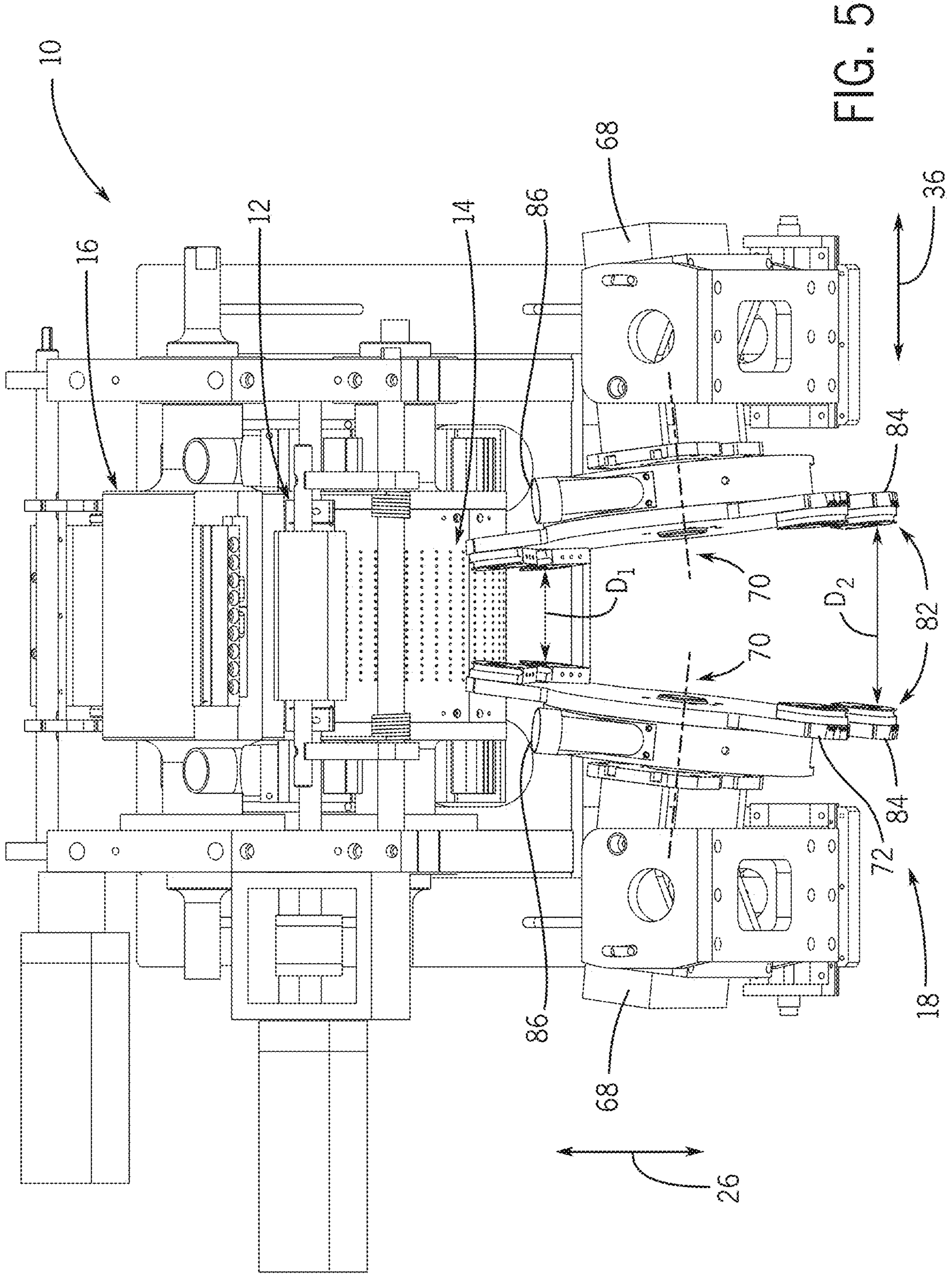
FIG. 5 illustrates top perspective view of a portion of the apparatus of FIG. 3, including a configuration of the stretch unit included therein, according to an embodiment of the invention.
Figure 6:
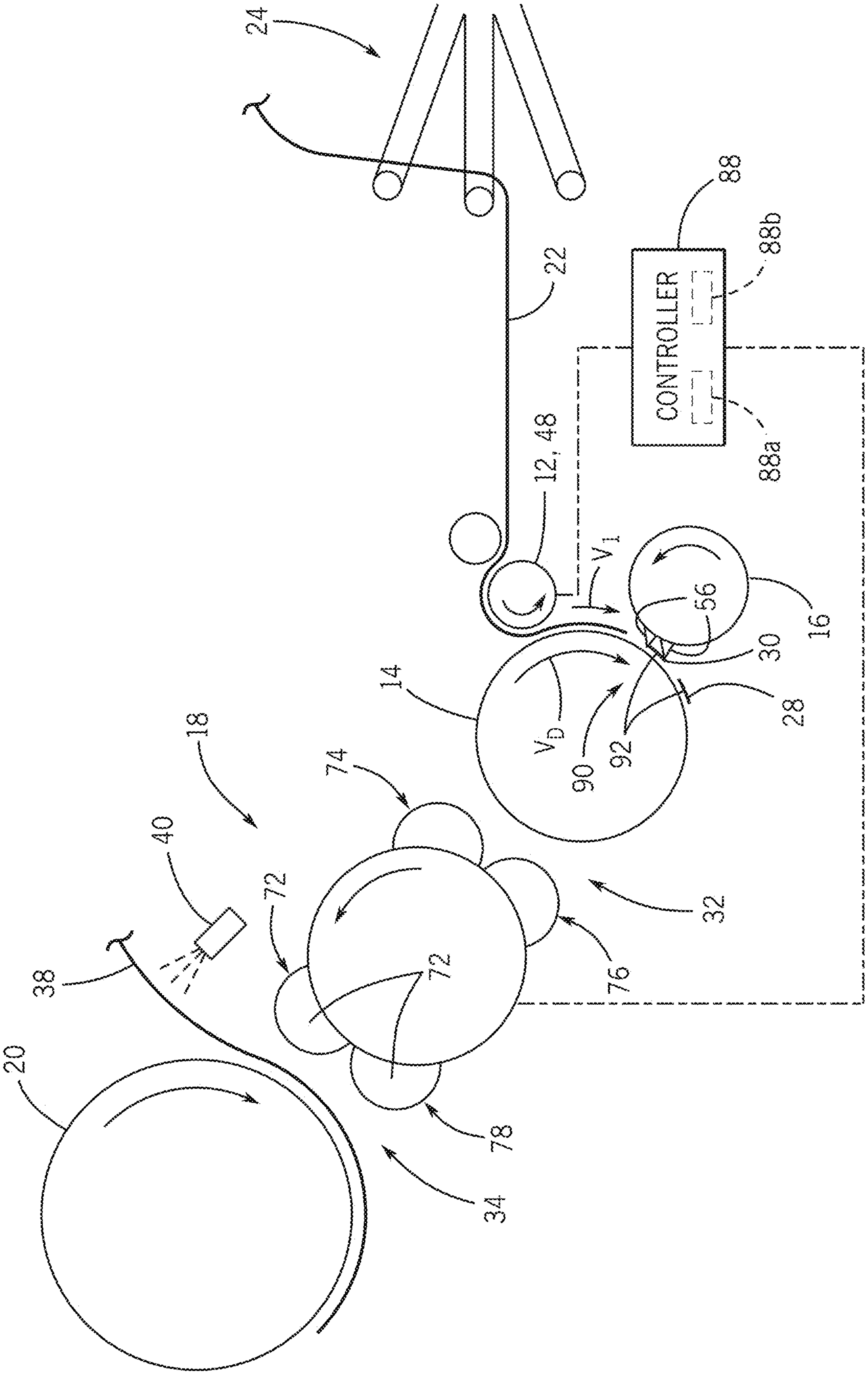
FIGS. 6-12 illustrate a method of forming, stretching, and applying discrete elastic film portions to a carrier web during various operational steps of the method, utilizing the apparatus of FIGS. 3-5, according to an embodiment of the invention.

The structure of the stretch unit 18 is shown in FIG. 4, and now also in FIG. 5, as being generally formed of two motorized wheels or discs 66 (i.e., wheels 66 that are rotationally driven by respective servo motors 68) that are spaced apart from one another in the cross-machine direction 36. The wheels 66 rotate about axes of rotation 70 that intersect with respect to each other at an intermediate point between the two wheels 66. In one embodiment, the stretch wheels 66 rotate about their axes 70 at a constant speed that is similar or identical to that of the vacuum drum 14 and the cutting unit 16. Mounted on each of the wheels 66 are arms 72 that each extend radially outward therefrom. In the illustrated embodiment, each wheel 66 includes four arms 72 mounted thereon. As referenced hereafter, an arm 72 on one wheel is aligned with a corresponding arm 72 on the opposite wheel to form a "pair of arms" that cooperate with each other to pick up an elastic film portion 28, 30 from the vacuum drum 14. Thus, the arms 72 are considered to provide/form a first pair of arms 74, a second pair of arms 76, a third pair of arms 78, and a fourth pair of arms 80. As seen in FIG. 4, the first pair of arms 74 and the second pair of arms 76 are positioned proximate each other on one side of the stretch unit 18 (i.e., on one side of the wheels 66), while the third pair of arms 78 and the fourth pair of arms 80 are positioned proximate each other on an opposite side of the stretch unit 18 (i.e., 180° from the first and second pairs of arms 74, 76).

At the end of each of the arms 72 is a gripping surface 82 intended to grip the ends of an elastic film portion 28, 30 and by which the elastic film portions may be picked up off of the vacuum drum 14 and retained in place while the elastic film portions 28, 30 are stretched in the cross-machine direction 36. In the illustrated embodiment, the gripping surface 82 exerts a gripping and retaining force on the ends of an elastic film portion 28, 30 by way of a vacuum, although it is recognized that a gripping and retaining force could instead be provided via a mechanical hooking or interference type structure (e.g., pins) provided on the gripping surface 82. For providing a vacuum force on the gripping surface 82, a series of openings 84 is formed in the gripping surface 82 through which a vacuum is provided. A pair of vacuum pipes 86 is provided in the stretch unit 18 that draws a vacuum into an interior vacuum chamber (not shown) of each wheel 66. The openings 84 on the gripping surface 82 of each arm 72 are in fluid communication with the interior vacuum chamber of their respective wheel 66 and, thus a vacuum may be drawn through the openings 84. At a pickup location 32 where an elastic film portion 28, 30 is drawn off of the vacuum drum 14, the ends of an elastic film portion 28, 30 are positioned relative to a respective pair of arms 72 of the stretch unit 18 such that the film portion 28, 30 covers the openings 84 of the gripping surface 82 of the arms 72, and thus the film portion 28, 30 is forced onto the gripping surface 82 with a vacuum gripping effect. An intensity of the vacuum force applied on the elastic film portions 28, 30 may be adjusted during operation of the stretch unit 18, such as by selectively operating a vacuum pump (not shown) that provides the vacuum within the wheels 66 (via pipes 86).

In operation of the stretch unit 18, the two wheels 66 are drawn in rotation by respective motors 68 driven by a controller 88 (FIG. 3). The controller 88 synchronizes operation of the motors 68 with respect to each other in such a manner to prevent an elastic film portion 28, 30 retained by a respective pair of arms 72 from ending up oblique due to a rotation speed difference of the wheels 66. As the wheels 66 rotate about their axes 70, the spacing of the arms 72 of each respective pair of arms 74, 76, 78, 80 will change in the cross-machine direction 36, either diverging or converging dependent on the angular position of the arms 72 about the axes of rotation. That is, the mutually inclined or angled arrangement of the axes 70 of the wheels 66 causes the peripheries of the wheels 66, and thus the trajectories travelled by the arms 72 thereon, to alternately diverge and converge in such a manner to be "close" when adjacent the vacuum drum 14 at a pickup location 32 and "apart" when adjacent the transfer drum 20/carrier web 38 at a transfer location 34. As best shown in FIG. 5, the arms 72 of a respective arm pair 74, 76, 78, 80 will be separated by a first distance D1 in the cross-machine direction 36 when adjacent the vacuum drum 14 at the pickup location 32 and separated by a second distance D2 in the cross-machine direction 36 that is greater than the first distance D1 when adjacent the transfer drum 20 and carrier web 38 at the transfer location 34, such that the pair of arms 74, 76, 78, 80 serve as drawing members that subject each elastic film portion 28, 30 to stretching as it moves from the pickup location 32 to the transfer location 34.

According to embodiments, the apparatus 10 is operated to form, stretch, and apply discrete elastic film portions 28, 30 to the carrier web 38, with the apparatus 10 being controlled in a manner that allows elastic film portions 28, 30 to be applied to the carrier web 38 with a varied pitch therebetween. Accordingly, in an example implementation, the apparatus 10 may be utilized in a process for forming absorbent articles where elastic film portions are to be applied as left and right elastic leg cuffs for the absorbent article, such as illustrated in FIGS. 2A and 2B.

Referring now to FIGS. 6-12, and with continued reference to FIGS. 3-5, a method for forming, stretching, and applying discrete stretched film portions 28, 30 to a carrier web 38 is shown, according to an embodiment of the invention. As first shown in FIG. 6, the drive roll 12 receives a continuous elastic film 22 that may be provided thereto via progression of the film by other rolls (not shown) and after passing over a dancer roll arrangement 24. Rotation of the drive roll 12 is controlled via the servo motor 48 and an associated controller, which in the illustrated embodiment is controller 88, although it may be a separate controller. The controller 88 and servo motor 48 operate the drive roll 12 to feed the continuous elastic film 22 to the vacuum drum 14 at a first feed rate V1. The feed rate V1 at which the continuous elastic film 22 is fed to the vacuum surface 62 of the rotating vacuum drum 14 is a lower speed as compared to the speed of the vacuum drum 14, which is moving at a constant, relatively higher surface speed, VD. The incoming continuous elastic film 22 is therefore allowed to "slip" across the surface 62 of the vacuum drum 14 for purposes of performing a slip-and-cut film cutting operation.

While the continuous elastic film 22 is being fed at the feed rate V1 and translated toward a cutting location 90 between the vacuum drum 14 and the cutting unit 16, the cutting unit 16 rotates into a position where the pair of cutting knives 56 thereon are brought into contact with the continuous elastic film 22. The cutting knives 56 are preferably moving at a speed similar or identical to that of the vacuum drum surface 62 (i.e., vacuum drum speed VD). The pair of cutting knives 56 perform a quick, successive pair of cuts on the continuous elastic film 22 to form a first film portion 28 and a second film portion 30 that are severed from the remainder of the continuous elastic film 22. The first film portion 28 and the second film portion 30 are collectively referred to hereafter as a first film portion pair 92.

Figure 7:
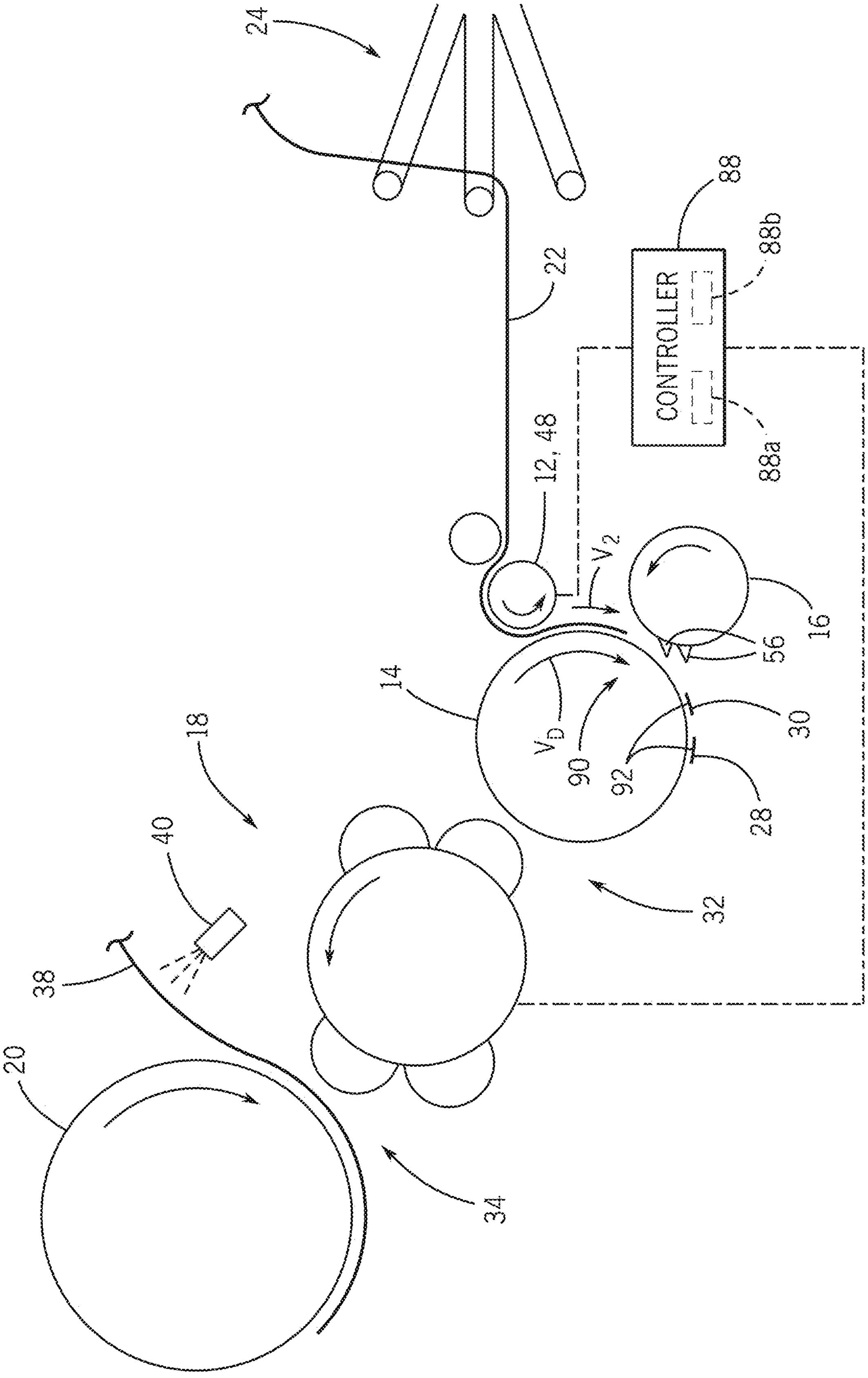

At approximately the same time as the cutting knives 56 are cutting the first film portion pair 92 from the remainder of the continuous elastic film 22 (i.e., either just prior to the cutting, during the cutting, or immediately after the cutting), the controller 88 and the servo motor 48 operate to control the drive roll 12 to reduce the feed rate at which the continuous elastic film 22 is fed to the vacuum drum 14. As shown in FIG. 7, the drive roll 12 operates to reduce the feed rate of the continuous elastic film 22 down to a second feed rate V2 that is less than the first feed rate V1. Reducing the feed rate of the continuous elastic film 22 down to the second feed rate V2 provides for the first film portion pair 92 to rotate further along the surface 62 of the vacuum drum 14 prior to the continuous elastic film 22 being again advanced to the cutting location 90 between the vacuum drum 14 and the cutting unit 16, such that the first film portion pair 92 will be spaced apart from the next or second film portion pair 94 that will be cut from the continuous elastic film 22 (i.e., another first film portion 28*b* and another second film portion 30*b* that will form the second film portion pair 94). While the continuous elastic film 22 is being fed to the vacuum drum 14 at the feed rate V2, the cutting unit 16 continues to rotate, with the pair of cutting knives 56 rotating about the cutting wheel 52 through a range of non-cutting positions.

Figure 8:
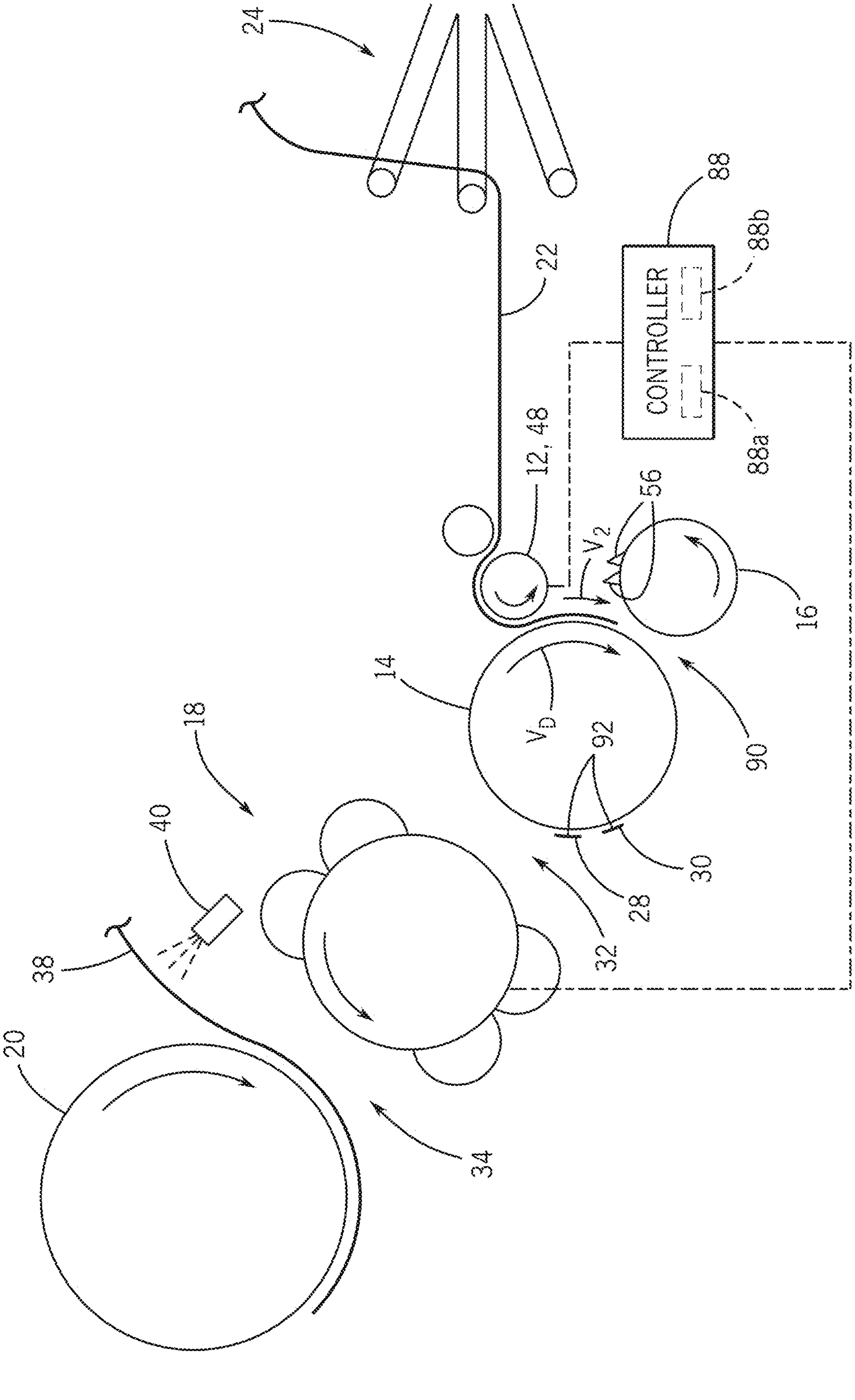

As shown now in FIG. 8, while the continuous elastic film 22 is being fed at the feed rate V2, the first film portion pair 92 has further rotated about the surface 62 of the vacuum drum 14 and the position of the cutting knives 56 is again approaching the cutting location 90 between the vacuum drum 14 and the cutting unit 16. However, because the continuous elastic film 22 has been fed at the lower feed rate V2 during this period, an appropriate length of continuous elastic film 22 that will provide for formation of a second film portion pair 94 has not yet reached the cutting location 90 between the vacuum drum 14 and the cutting unit 16. At this time, a determination is made by the controller 88 as to when the feed rate of the continuous elastic film 22 should be increased for the continuous elastic film 22 to again be fed to the vacuum drum 14 at the feed rate V1. The determination by the controller 88 may be either a time-based determination or a measurement-based determination, according to embodiments. That is, the controller 88 may cause the drive roll 12, via operation of the servo motor 48, to again convey the continuous elastic film 22 at the feed rate V1 after a pre-determined period of time (as monitored by the controller 88) has passed with the drive roll 12 operating at the feed rate V2 or after a certain length of the continuous elastic film 22 has been conveyed in the machine direction 26 (such as measured by an associated sensor and relayed to the controller 88) with the drive roll 12 operating at the feed rate V2. For performing the determination(s) described above, the controller 88 may include a processor 88*a* and memory 88*b*, where the processor 88*a* performs the computation and control functions of the controller 88 via executing one or more programs which may be contained within the memory 88*b*, and with the memory 88*b* contained therein stored values (such as the pre-determined time period of film length) and programs for execution.

Figure 9:
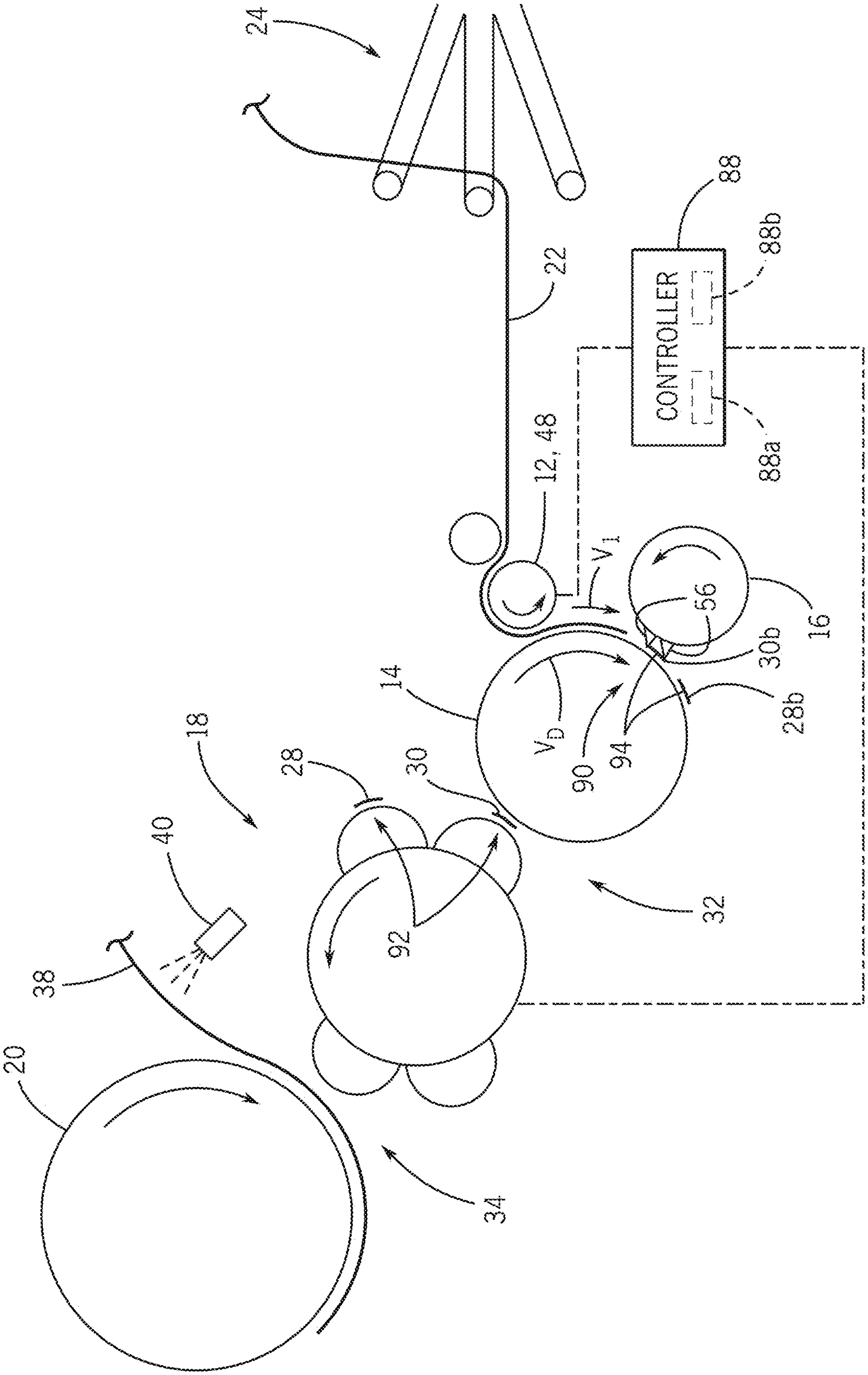

Upon a determination by the controller 88 that the drive roll 12 is to revert back to conveying the continuous elastic film 22 to the vacuum drum 14 at the feed rate V1, the controller 88 may control operation of the servo motor 48 to cause the drive roll 12 to again convey the continuous elastic film 22 to the vacuum drum 14 at the feed rate V1. Referring now to FIG. 9, the controller 88 is now operating the servo motor 48 to cause the drive roll 12 to feed the continuous elastic film 22 to the vacuum drum 14 at the first feed rate V1. While the continuous elastic film 22 is being fed at the feed rate V1 and translated toward the cutting location 90, the cutting unit 16 is again rotating into position where the pair of cutting knives 56 thereon are brought into contact with the continuous elastic film 22 to form another first film portion 28*b* and another second film portion 30*b* (i.e., the second film portion pair 94) that are severed from the remainder of the continuous elastic film 22, according to a slip-and-cut film cutting operation as previously described.

At about the same time as the cutting of the second film portion pair 94 is occurring, the first film portion pair 92 is arriving at the pickup location 32 where the first and second film portions 28, 30 are drawn off the vacuum drum 14 by the stretch unit 18. That is, the first pair of arms 74 and the second pair of arms 76 are rotated into position so as to be adjacent the pickup location 32 at the same time that the first film portion pair 92 is arriving at the pickup location 32. The first film portion 28 is drawn off the vacuum drum 14 by the first pair of arms 74 and, sequentially thereafter, the second film portion 30 is drawn off the vacuum drum 14 by the second pair of arms 76. In drawing each of the first and second film portions 28, 30 off the vacuum drum 14, the arms 72 in each of the first and second pairs or arms 74, 76 are positioned in a "close" arrangement (separated by a distance D1, FIG. 5), such that the gripping surface 82 on the radially outward end of each arm 72 is positioned adjacent a respective end (in the crosswise direction) of the film portion 28, 30 that is to be picked up thereby. As indicated previously, the film portions 28, 30 are then retained on the gripping surface 82 of the arms 72, such as via a vacuum communicated through openings 84 formed in the gripping surface 82, with the first film portion 28 spanning between the arms 72 of the first arm pair 74 and the second film portion 30 spanning between the arms 72 of the second arm pair 76.

Figure 10:
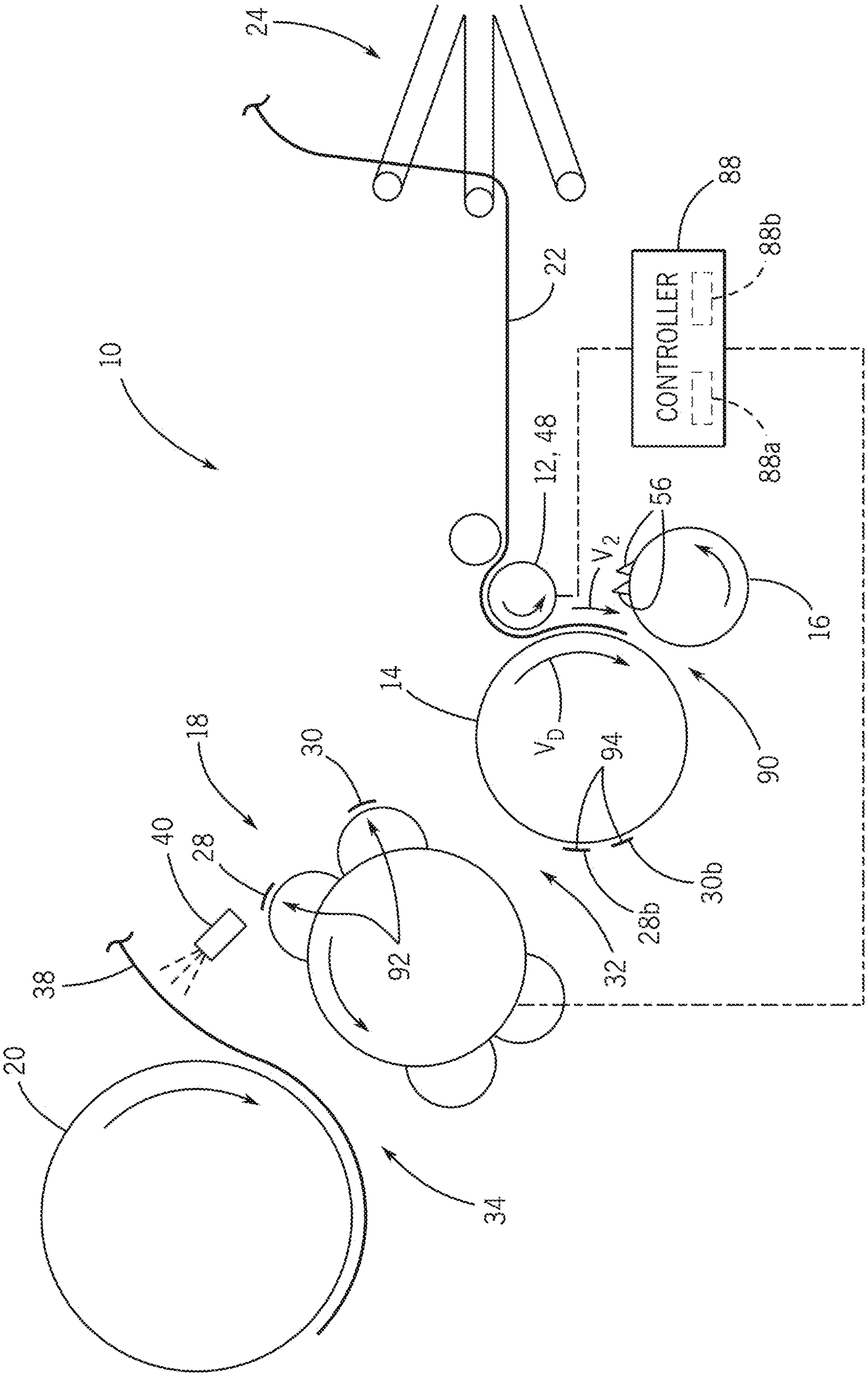

At approximately the same time as the second film portion pair 94 has been cut from the continuous elastic film 22 and as the first film portion pair 92 has been picked up by the first and second pairs of arms 74, 76 of the stretch unit 18, the controller 88 and the servo motor 48 operate to control the drive roll 12 to again provide the continuous elastic film 22 to the vacuum drum 14 at the lower second feed rate V2. While this occurs, and during continued operation of the apparatus with the drive roll 12 feeding the continuous elastic film 22 to the vacuum drum 14 at the feed rate V2, the second film portion pair 94 rotates further along the surface of the vacuum drum 14 toward the pickup location 32 and the first film portion pair 92 continues to rotate on the stretch unit 18 from the pickup location 32 toward the transfer location 34 while being retained on the first and second pairs of arms 74, 76, as shown in FIG. 10. As the first film portion pair 92 rotates on the stretch unit 18 toward the transfer location 34, each of the first pair of arms 74 and the second pair of arms 76 begin to separate in the cross-machine direction 36 in order to stretch the first and second film portions 28, 30, respectively. That is, as the first and second pairs of arms 74, 76 rotate on the stretch unit 18 from the pickup location 32 to the transfer location 34, the separation between the arms 72 in each arm pair 74, 76 increases from a first distance D1 in the cross-machine direction 36 to a second distance D2 in the cross-machine direction 36 (see FIG. 5), so as to stretch the first and second film portions 28, 30 in the cross-machine direction 36.

Figure 11:
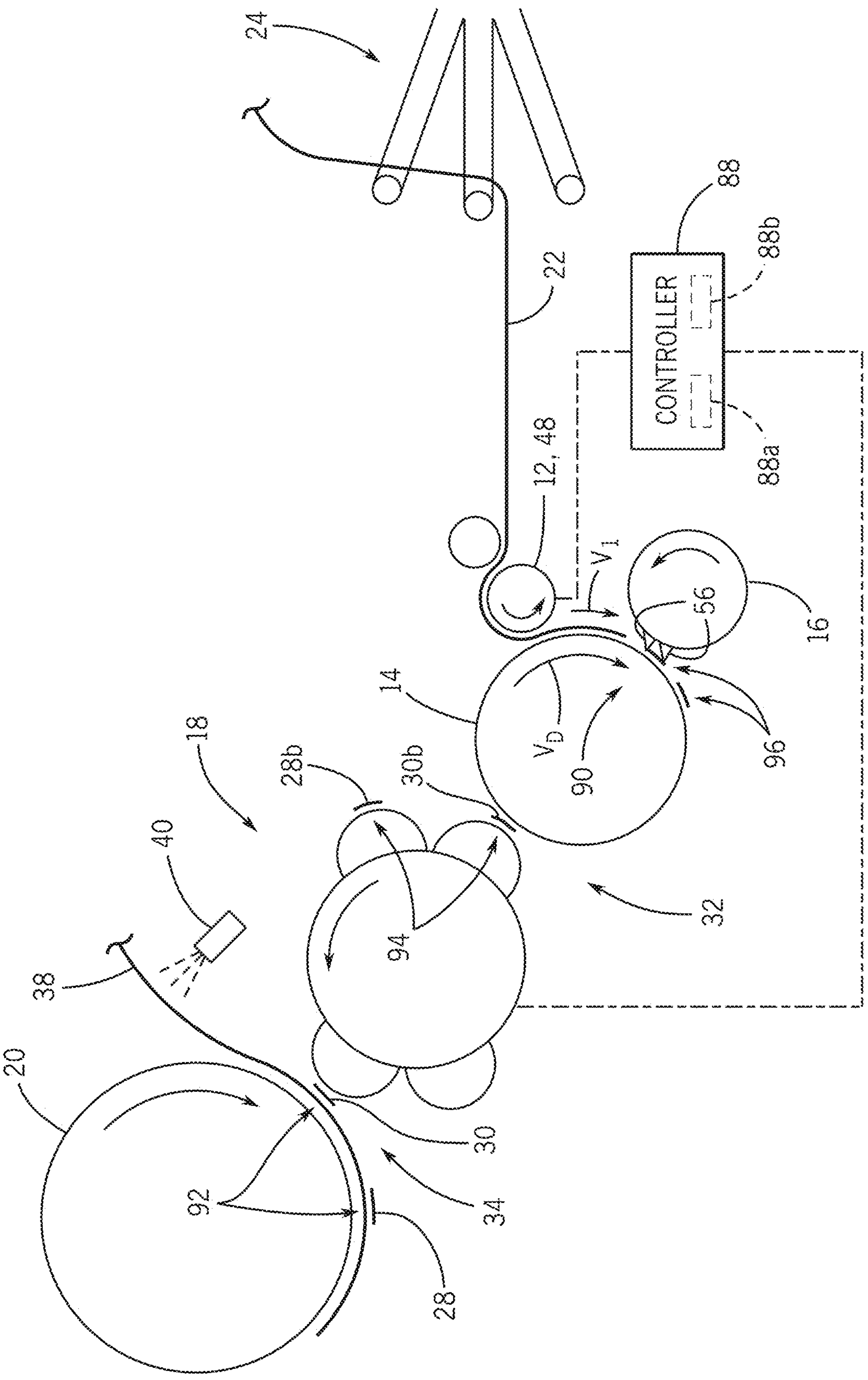

As shown in FIG. 11, upon the stretch unit 18 rotating such that the first film portion pair 92 reaches the transfer location 34, the first and second film portions 28, 30 are deposited onto the carrier web 38 by the first and second pairs of arms 74, 76 of the stretch unit 18. With the arms 72 in each of the first and second pairs of arms 74, 76 being positioned in an "apart" arrangement (separated by distance D2, FIG. 5) when they arrive at the transfer location 34, the first and second film portions 28, 30 are deposited onto the carrier web 38 while in a stretched state. As previously indicated, the first and second film portions 28, 30 are deposited onto the carrier web 38 at locations where adhesive has been previously applied, such that the film portions 28, 30 are retained in place on the carrier web 38 after being deposited thereon. The presence of the transfer drum 20 on the opposite side of the carrier web 38 from the stretch unit 18 facilitates the transfer of the stretched first and second film portions 28, 30 onto the carrier web 38, with the transfer drum 20 enabling the stretched first and second film portions 28, 30 to be securely positioned on the adhesive.

As also shown in FIG. 11, in conjunction with the first film portion pair 92 reaching the transfer location 34, the second film portion pair 94 has rotated about the vacuum drum 14 to reach the pickup location 32. As previously described regarding the first film portion pair 92, the first and second film portions 28*b*, 30*b* of the second film portion pair 94 are drawn off the vacuum drum 14 by the stretch unit 18 upon arriving at the pickup location 32. To perform the pickup off the vacuum drum 14, the third pair of arms 78 and the fourth pair of arms 80 of the stretch unit 18 are rotated into position so as to be adjacent the pickup location 32 at the same time that the second film portion pair 94 is arriving at the pickup location 32. The first film portion 28*b* is drawn off the vacuum drum 14 by the third pair of arms 78 and, sequentially thereafter, the second film portion 30*b* is drawn off the vacuum drum 14 by the fourth pair of arms 80. In drawing the second film portion pair 94 off the vacuum drum 14, the arms 72 in each of the third and fourth arm pairs are positioned in a "close" arrangement (separated by distance D1, FIG. 5), such that the gripping surface 82 on the radially outward end of each arm 72 is positioned adjacent a respective end (in the crosswise direction) of the film portion 28*b*, 30*b* that is to be picked up thereby. As indicated previously, the film portions 28*b*, 30*b* are then retained on the gripping surface 82 of the arms, such as via a vacuum communicated through openings 84 formed in the gripping surface 82, with the first film portion 28*b* spanning between the arms 72 of the third arm pair 78 and the second film portion 30*b* spanning between the arms 72 of the fourth arm pair 80.

At approximately the same time that the first film portion pair 92 reaches the transfer location 34 and the second film portion pair 94 reaches the pickup location 32, a determination is made by the controller 88 as to whether the drive roll 12 should transition from conveying the continuous elastic film 22 to the vacuum drum 14 at the feed rate V2 back to conveying the continuous elastic film 22 to the vacuum drum 14 at the feed rate V1. As previously described, the determination made by the controller 88 may be either a time-based determination or a measurement-based determination, with the controller 88 causing the drive roll 12 to again convey the continuous elastic film 22 to the vacuum drum 14 at the feed rate V1 upon either a predetermined period of time having passed or a certain length of the continuous elastic film 22 having been conveyed in the machine direction 26.

Figure 12:
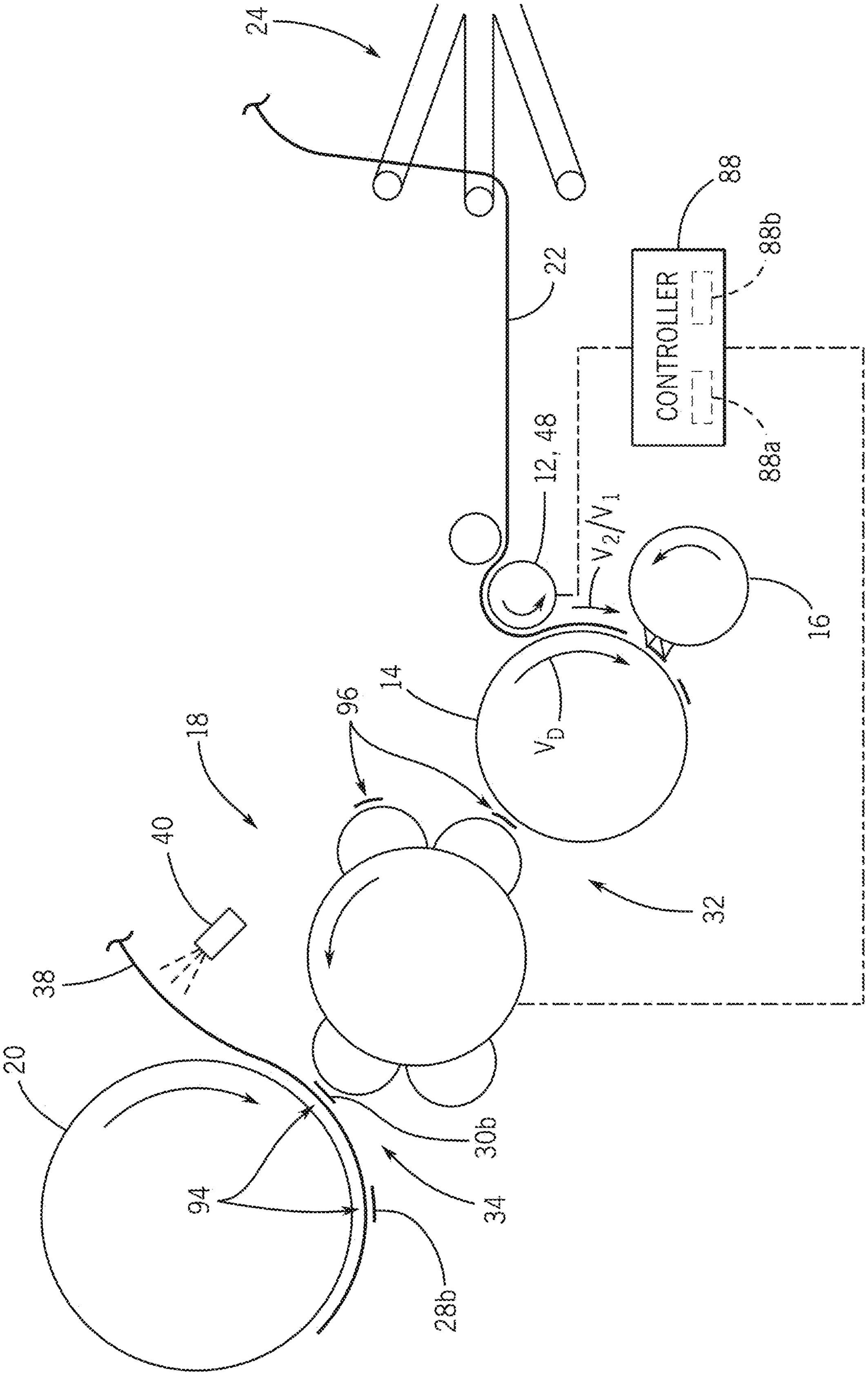

Referring now to FIG. 12, the second film portion pair 94 is shown as now having rotated about the stretch unit 18 to arrive at the transfer location 34. During this time a feed rate change (from V1 back to V2) has been performed and a third film portion pair 96 has been cut from the continuous elastic film 22. Upon reaching the transfer location 34, the first and second film portions 28*b*, 30*b* of the second film portion pair 94 are deposited onto the carrier web 38 by the third and fourth pairs of arms 78, 80 of the stretch unit 18. With the arms 72 in each of the third and fourth pairs of arms 78, 80 positioned in an apart arrangement (separated by distance D2, FIG. 5B) when they arrive at the transfer location 34, the first and second film portions 28*b*, 30*b* are deposited onto the carrier web 38 while in a stretched state. As previously indicated, the first and second film portions 28*b*, 30*b* are deposited onto the carrier web 38 at locations where adhesive has been previously applied, such that the film portions 28*b*, 30*b* are retained in place on the carrier web 38 after being deposited thereon.

By performing the operational steps of the method illustrated in FIGS. 6-12, the pitch between discrete stretched elastic film portions 28, 30, 28*b*, 30*b* applied to the carrier web 38 is varied in a desired manner and by a desired amount. Specifically, by selectively controlling the feed rate at which the drive roll 12 feeds the continuous elastic film 22 to the vacuum drum 14, i.e., switching the feed rate between the first feed rate V1 and the second feed rate V2, the pitch between successive pairs of film portions (first film portion pair 92 and second film portion pair 94) cut from the continuous elastic film 22 can be controlled.

Figure 13:
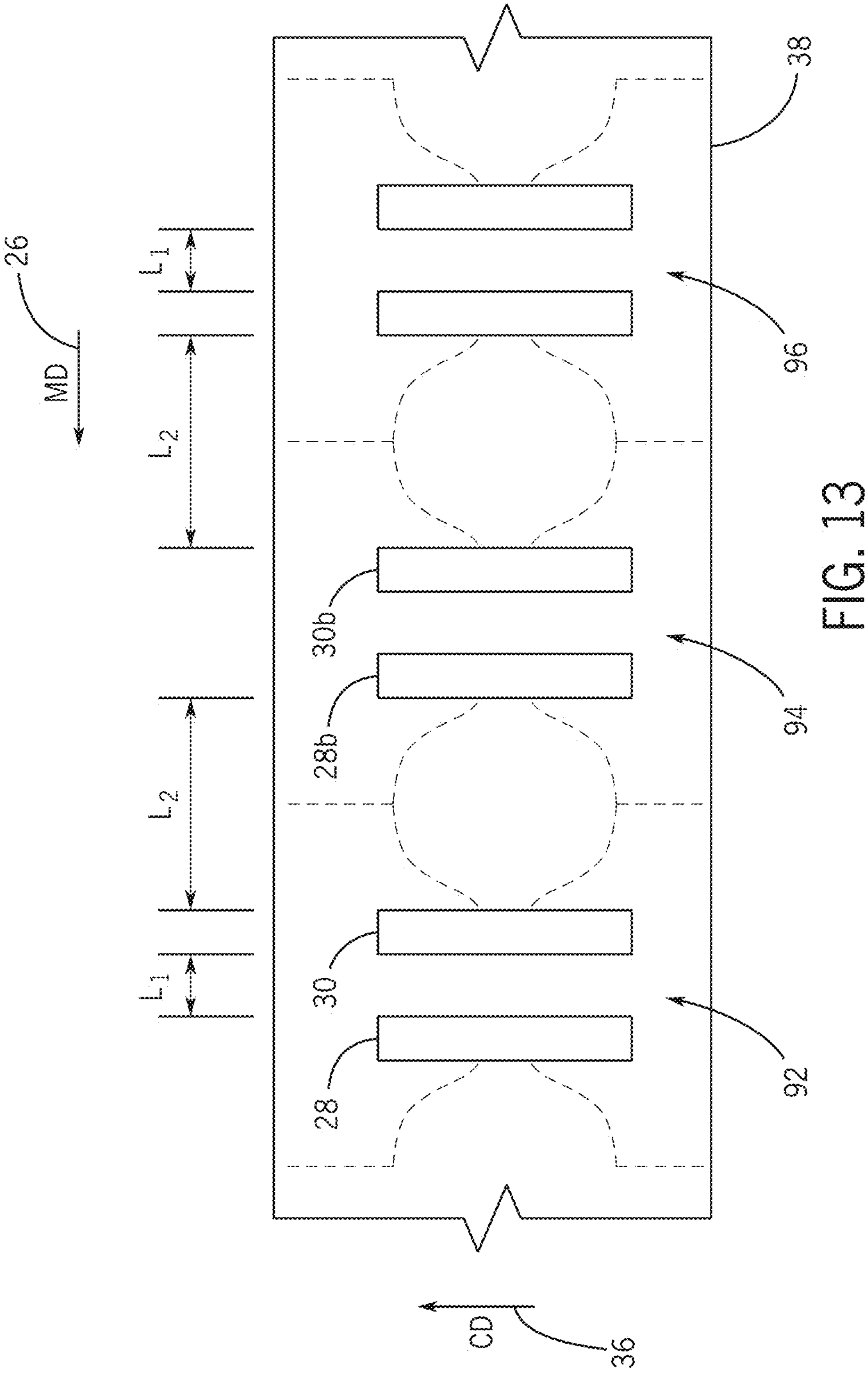
FIG. 13 illustrates the positioning of a plurality of discrete stretched film portions on a carrier web for an example article configuration, achieved via the method of FIGS. 6-12, according to an embodiment of the invention.
Figure 14:
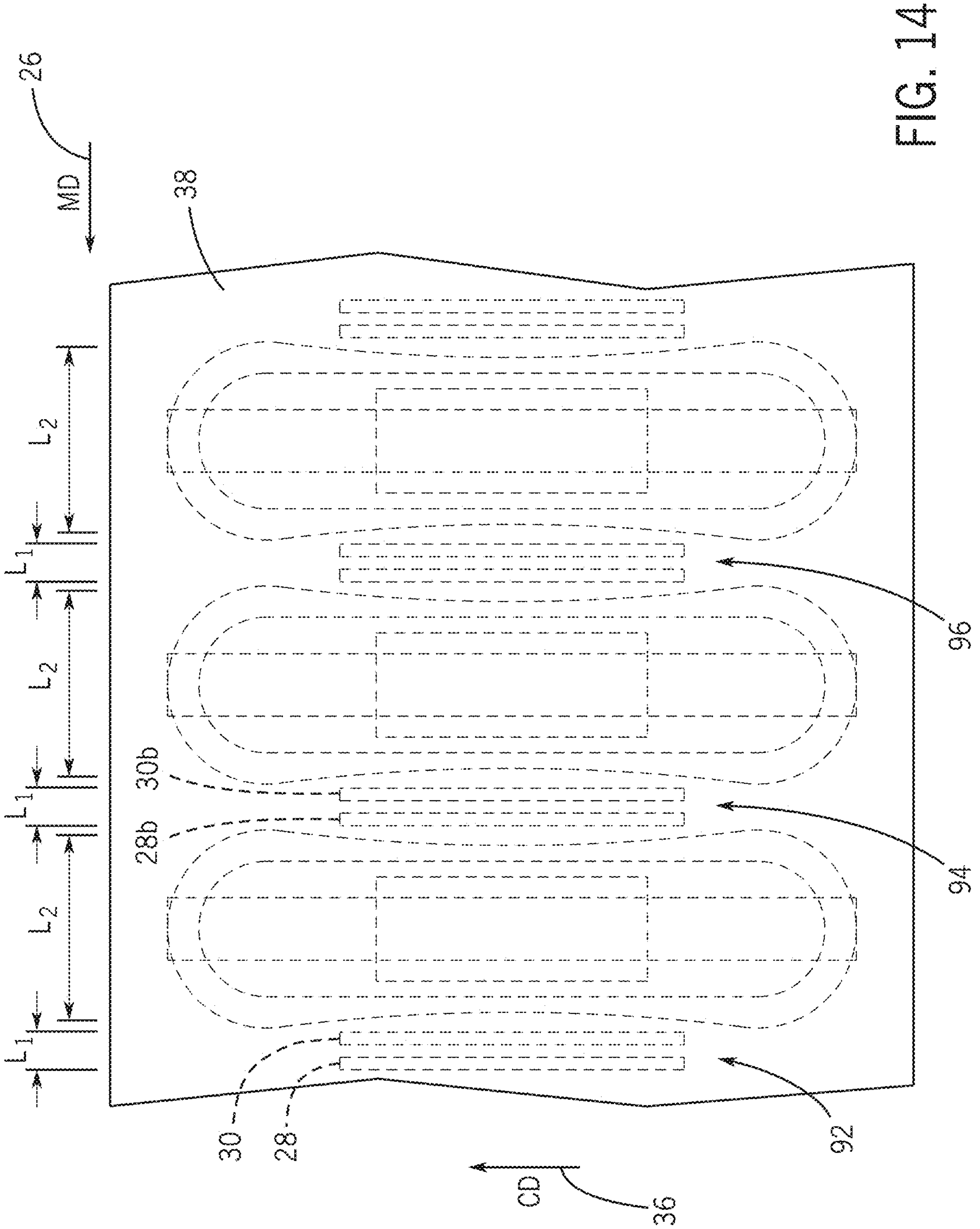
FIG. 14 illustrates the positioning of a plurality of discrete stretched film portions on a carrier web for another example article configuration, achieved via the method of FIGS. 6-12, according to an embodiment of the invention.

The varying of the pitch between cut elastic film portions 28, 30, 28*b*, 30*b* applied onto the carrier web 38 can best be seen in FIGS. 13 and 14, with the elastic film portions 28, 30, 28*b*, 30*b* arranged on the carrier web 38 for different product configurations. As shown therein, for a series of discrete first film portions 28, 28*b* and discrete second film portions 30, 30*b* that are applied onto the carrier web 38, the first film portion 28 and the second film portion 30 in a first film portion pair 92 are separated from one another by a first distance in the machine direction, L1. As previously described, the first film portion 28 and the second film portion 30 in the first film portion pair 92 are applied onto the carrier web 38 by the first and second pairs of arms 74, 76 of the stretch unit 18, with the distance or pitch L1 between the first film portion 28 and the second film portion 30 being determined based on the separation between the first and second pairs of arms 74, 76 on the stretch unit 18. Similar to the first film portion pair 92, the (another) first film portion 28*b* and the (another) second film portion 30*b* in the second film portion pair 94 are also separated from one another by the first distance in the machine direction, L1. The (another) first film portion 28*b* and the (another) second film portion 30*b* in the second film portion pair 94 are applied onto the carrier web 38 by the third and fourth pairs of arms 78, 80 of the stretch unit 18, with the distance L1 between the (another) first film portion 28*b* and the (another) second film portion 30*b* being determined based on the separation between the third and fourth pairs of arms 78, 80 on the stretch unit 18.

While the distance L1 between the film portions in the first film portion pair 92 and between the film portions in the second film portion pair 94 is a distance L1, the distance or pitch between the first film portion pair 92 and the second film portion pair 94 (and between the second film portion pair 94 and third film portion pair 96) is an increased distance, L2. As previously indicated, the increased distance (L2) between the first film portion pair 92 and the second film portion pair 94 as compared to the distance (L1) between the first and second film portions 28, 30, 28*b*, 30*b* within each film portion pair results from the feed rate of the continuous elastic film 22 being lowered to the feed rate V2 (from the higher feed rate V1) for at least a majority of a period between when the first film portion pair 92 is cut and when the second film portion pair 94 is cut. By operating the drive roll 12 to decrease the feed rate during this period, the first film portion pair 92 is allowed to separate further in the machine direction from the second film portion pair 94, thereby resulting in the increased distance or pitch L2.

As shown in FIG. 13, the positioning of the discrete stretched elastic film portions 28, 30, 28*b*, 30*b* on the carrier web 38 may correspond to the position of elastic leg cuffs 114 that are to be provided for a series of absorbent articles that are being manufactured according to a continuous process, such as the pants-type article 110 shown in FIG. 2B for example. The first and second film portions 28, 30, 28*b*, 30*b* in a film portion pair form the left and right elastic cuff members of one absorbent article and are spaced apart by the distance L1 accordingly. Furthermore, the film portion pair 92 (left and right elastic cuff members) of one absorbent article is separated from the film portion pair 94 (left and right elastic cuff members) of a next/adjacent absorbent article by the distance L2. It is recognized that the distances L1 and L2 will depend on the sizing of the absorbent article being manufactured, as determined by a desired/required spacing or pitch between the left and right elastic cuff members and a desired/required spacing or pitch between adjacent absorbent articles.

FIG. 14 shows the positioning of the discrete stretched elastic film portions 28, 30, 28*b*, 30*b* on the carrier web 38 as corresponding to the position of elastic leg cuffs 114 that are provided for a series of light incontinence absorbent articles (e.g., the light incontinence article 100 shown in FIG. 2A) that are manufactured according to a continuous process. The first and second film portions 28, 30, 28*b*, 30*b* in each film portion pair 92, 94, 96 are spaced apart by the distance L1, while the film portion pair 92 is separated from the film portion pair 94 and the film portion pair 94 is separated from the film portion pair 96 by the distance L2. The first and second film portions 28, 30, 28*b*, 30*b* in each film portion pair 92, 94, 96 form elastic cuff members of adjacent absorbent articles, e.g., the first and second film portions 28, 30 of film portion pair 92 form a right and left elastic cuff member in adjacent articles and the first and second film portions 28*b*, 30*b* of film portion pair 94 form a right and left elastic cuff member in adjacent articles, with a cut being made between the first and second film portions 28, 30, 28*b*, 30*b* in a film portion pair (between portions 28, 30 and between 28*b*, 30*b*) to form discrete articles. It is recognized that the distances L1 and L2 will depend on the sizing of the absorbent article being manufactured, as determined by a desired/required spacing or pitch between the left and right elastic cuff members and a desired/required spacing or pitch between adjacent absorbent articles.

According to embodiments, the distances L1 and L2 could be varied via reconfiguring of the apparatus 10 shown and described in FIGS. 3-5, such as by repositioning of the stretch unit arms 72 on the stretch wheel 66 or reconfiguring of the cutting unit 16, etc., and/or by changing the feed rates at which the continuous elastic film 22 is fed to the vacuum drum 14. Furthermore, it is recognized that an alternative stretch wheel could be provided in the apparatus 10 that allows for variation of the L1 and/or L2 distances. For example, while the stretch unit 18 in FIGS. 4 and 5 is described as being constructed as generally including two wheels 66 each driven by an associated servo motor 68, and with each wheel 66 including four arms 72 thereon arranged so as to be on opposite sides of the wheel (so that first and second pairs of arms 74, 76 are fixedly positioned 180° apart from the third and fourth pairs of arms 78, 80), it is recognized that alternative constructions of the stretch unit 18 could be provided where the angular positioning of the first and second pairs of arms 74, 76 relative to the third and fourth pairs of arms 78, 80 could be varied. In such an embodiment, additional stretch wheels and servo motors could be provided in the stretch unit that allow for rotation and positioning of the first and second pairs of arms 74, 76 to be separately controlled from rotation and positioning of the third and fourth pairs of arms 78, 80. Such a construction of the stretch unit would allow for the distance L2 to be varied when applying film portions onto the carrier web, such as when a product size change for the absorbent article is to be implemented.

Beneficially, embodiments of the invention thus provide a method and apparatus for forming, stretching, and applying elastic film portions or segments onto a carrier web, such as might be employed for elastic leg cuffs in the manufacture of an absorbent article. By selectively controlling the feed rate at which a continuous elastic film is fed in the machine direction for cutting, stretching, and application of elastic segments formed therefrom, the spacing between the elastic segments applied onto the carrier web can be varied in a desired manner. The pair of elastic segments or cuffs for a first absorbent article can be spaced apart on the carrier web by a desired first distance, while the pair of elastic segments or cuffs for a next absorbent article can be spaced apart from the pair of elastic segments or cuffs for the first absorbent article by a desired second distance that is greater than the first distance. The method apparatus provides for the formation and application of left and right elastic leg cuffs for each absorbent article with this varied pitch using only a single cutting unit and stretch unit, so as to minimize hardware costs in the apparatus.

Therefore, according to one embodiment of the invention, a method of applying discrete stretched film portions to a carrier web includes conveying a continuous elastic film in a machine direction (MD), operating a cutting unit to cut the continuous elastic film into a series of discrete first film portions and discrete second film portions, selectively adjusting a feed rate of the continuous elastic film upstream of the cutting unit, transferring a first film portion of the series of discrete first film portions from a vacuum drum to a first pair of arms of a stretch unit, and transferring a second film portion of the series of discrete second film portions from the vacuum drum to a second pair of arms of the stretch unit. The method also includes stretching the first film portion in a cross-machine direction (CD) by separating the first pair of arms in the CD as the stretch unit rotates from a pickup position to a transfer position, stretching the second film portion in the CD by separating the second pair of arms in the CD as the stretch unit rotates from the pickup position to the transfer position, and transferring the stretched first and second film portions from the stretch unit to the carrier web.

According to another embodiment of the invention, an apparatus for applying stretched elastic segments to a carrier web includes a drive roll configured to feed a continuous elastic film in a machine direction (MD), a vacuum drum positioned to receive the continuous elastic film from the drive roll, and a cutting unit positioned adjacent the vacuum drum and configured to cut the continuous elastic film to create a series of discrete first film portions and discrete second film portions. The apparatus also includes a stretch unit to transfer the series of discrete first film portions and discrete second film portions from a pickup position off the vacuum drum to a transfer position onto the carrier web, with the stretch unit further including a first pair of arms configured to transfer a first film portion of the series of discrete first film portions from the vacuum drum, the first pair of arms being separable in a cross-machine direction (CD) and a second pair of arms configured to transfer a second film portion of the series of discrete second film portions from the vacuum drum, the second pair of arms being separable in the CD, wherein each of the first pair of arms and the second pair of arms separate outwardly in the CD as they move from the pickup position to the transfer position, to stretch the first film portion and the second film portion, respectively, in the CD. The drive roll is operable to variably feed the continuous elastic film onto the vacuum drum at a first feed rate and a second feed rate that is slower than the first feed rate.

According to still another embodiment of the invention, a method of applying discrete stretched film portions to a carrier web includes operating a drive roll to feed a continuous elastic film in a machine direction (MD) onto a vacuum drum and operating a cutting unit to form a series of discrete first film portions and discrete second film portions from the continuous elastic film. The method also includes operating a stretch unit comprising a plurality of pairs of arms to rotatably transfer the series of discrete first film portions and discrete second film portions from a pickup position off the vacuum drum to a transfer position onto the carrier web, with each pair of arms of the plurality of pairs of arms securing a respective first film portion or second film portion thereto, stretch each respective first film portion and second film portion in a cross-machine direction (CD) by separating each pair of arms of the plurality of pairs of arms in the CD between the pickup position and the transfer position, and deposit the series of discrete first film portions and discrete second film portions onto the carrier web at the transfer position. A first film portion and a second film portion of a first film portion pair deposited on the carrier web are separated in the MD by a first distance and a second film portion pair, including an another first film portion and an another second film portion, deposited on the carrier web is separated in the MD from the first film portion pair by a second distance greater than the first distance.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A method of applying discrete stretched film portions to a carrier web, the method comprising:

conveying a continuous elastic film in a machine direction (MD);

operating a cutting unit to cut the continuous elastic film into a series of discrete first film portions and discrete second film portions;

selectively adjusting a feed rate of the continuous elastic film upstream of the cutting unit;

transferring a first film portion of the series of discrete first film portions from a vacuum drum to a first pair of arms of a stretch unit;

transferring a second film portion of the series of discrete second film portions from the vacuum drum to a second pair of arms of the stretch unit;

stretching the first film portion in a cross-machine direction (CD) by separating the first pair of arms in the CD as the stretch unit rotates from a pickup position to a transfer position;

stretching the second film portion in the CD by separating the second pair of arms in the CD as the stretch unit rotates from the pickup position to the transfer position; and transferring the stretched first and second film portions from the stretch unit to the carrier web.

2. The method of claim 1, further comprising:

operating a drive roll to feed the continuous elastic film onto the vacuum drum at a first feed rate;

cutting the continuous elastic film with the cutting unit while the continuous elastic film is being fed at the first feed rate, to form a first film portion pair including the first film portion and the second film portion; and subsequent to forming the first film portion pair, operating the drive roll to feed the continuous elastic film onto the vacuum drum at a second feed rate that is lower than the first feed rate.

3. The method of claim 2, further comprising:

operating the drive roll to feed the continuous elastic film onto the vacuum drum at the second feed rate for a pre-determined time period or for a pre-determined length of the continuous elastic film;

operating the drive roll to feed the continuous elastic film onto the vacuum drum at the first feed rate after the pre-determined time period has passed or after the pre-determined length of the continuous elastic film has been fed; and cutting the continuous elastic film with the cutting unit while the continuous elastic film is being fed at the first feed rate, to form a second film portion pair including another first film portion of the series of discrete first film portions and another second film portion of the series of discrete second film portions.

4. The method of claim 3, further comprising:

transferring the another first film portion from the vacuum drum to a third pair of arms of the stretch unit;

transferring the another second film portion from the vacuum drum to a fourth pair of arms of the stretch unit;

stretching the another first film portion in the CD by separating the third pair of arms in the CD as the stretch unit rotates from the pickup position to the transfer position;

stretching the another second film portion in the CD by separating the fourth pair of arms in the CD as the stretch unit rotates from the pickup position to the transfer position; and transferring the stretched another first and second film portions from the stretch unit to the carrier web.

5. The method of claim 4, wherein in transferring the stretched first and second film portions and in transferring the stretched another first and second film portions, the method comprises spacing the stretched first and second film portions of the first film portion pair apart on the carrier web in the MD by a first distance and spacing the stretched another first and second film portions of the second film portion pair apart on the carrier web in the MD by the first distance.

6. The method of claim 5, wherein in transferring the stretched first and second film portions and in transferring the stretched another first and second film portions, the method comprises spacing the first film portion pair on the carrier web apart from the second film portion pair in the MD by a second distance greater than the first distance.

7. The method of claim 4, wherein transferring the first and second film portions and transferring the another first and second first film portions from the vacuum drum comprises:

rotating the stretch unit to position the first pair of arms and the second pair of arms adjacent the vacuum drum to remove the first and second film portions from the vacuum drum; and rotating the stretch unit to position the third pair of arms and the fourth pair of arms adjacent the vacuum drum to remove the another first and second film portions from the vacuum drum.

8. The method of claim 7, wherein the stretch unit is rotated at a constant speed.

9. The method of claim 3, comprising providing rotational power to the drive roll via a servo motor to selectively cause the drive roll to feed the continuous elastic film onto the vacuum drum at the first feed rate or the second feed rate.

10. The method of claim 3, wherein the cutting unit comprises a rotating cutting wheel having a first cutting element and a second cutting element fixedly positioned thereon so as to be proximate each other on the rotating cutting wheel, and wherein operating the cutting unit comprises:

performing a pair of cuts with the first and second cutting elements to form the first film portion and the second film portion;

rotating the rotating cutting wheel a full revolution; and performing another pair of cuts with the first and second cutting elements to form the another first film portion and the another second film portion.

11. The method of claim 1, further comprising rotating the vacuum drum at a drum speed that is higher than the first feed rate and the second feed rate at which the continuous elastic film is fed onto the vacuum drum, such that a leading edge of the continuous elastic film slips over a surface of the vacuum drum as it is fed onto the vacuum drum.

12. An apparatus for applying stretched elastic segments to a carrier web, the apparatus comprising:

a drive roll configured to feed a continuous elastic film in a machine direction (MD);

a vacuum drum positioned to receive the continuous elastic film from the drive roll;

a cutting unit positioned adjacent the vacuum drum and configured to cut the continuous elastic film to create a series of discrete first film portions and discrete second film portions; and a stretch unit to transfer the series of discrete first film portions and discrete second film portions from a pickup position off the vacuum drum to a transfer position onto the carrier web, the stretch unit comprising:

a first pair of arms configured to transfer a first film portion of the series of discrete first film portions from the vacuum drum, the first pair of arms being separable in a cross-machine direction (CD); and a second pair of arms configured to transfer a second film portion of the series of discrete second film portions from the vacuum drum, the second pair of arms being separable in the CD;

wherein each of the first pair of arms and the second pair of arms separate outwardly in the CD as they move from the pickup position to the transfer position, to stretch the first film portion and the second film portion, respectively, in the CD; and wherein the drive roll is operable to variably feed the continuous elastic film onto the vacuum drum at a first feed rate and a second feed rate that is slower than the first feed rate.

13. The apparatus of claim 12, further comprising:

a servo motor configured to selectively drive the drive roll to feed the continuous elastic film onto the vacuum drum at one of the first feed rate and the second feed rate; and a controller operably connected to the servo motor to control operation of the servo motor.

14. The apparatus of claim 13, wherein the controller is configured to:

operate the servo motor to cause the drive roll to feed the continuous elastic film onto the vacuum drum at the first feed rate for either a first pre-determined period of time or a first pre-determined length of the continuous elastic film; and operate the servo motor to cause the drive roll to feed the continuous elastic film onto the vacuum drum at the second feed rate for either a second pre-determined period of time or a second pre-determined length of the continuous elastic film;

wherein the servo motor is operated to cause the drive roll to alternately feed the continuous elastic film onto the vacuum drum at the first and second feed rates during ongoing operation.

15. The apparatus of claim 14, wherein the cutting unit comprises:

a rotating cutting wheel; and a first cutting element and a second cutting element affixed to the rotating cutting wheel;

wherein the first cutting element and the second cutting element are positioned proximate each other on one side of the rotating cutting wheel.

16. The apparatus of claim 15, wherein the controller is configured to coordinate rotation of the rotating cutting wheel with operation of the servo motor, such that the first and second cutting elements are positioned to cut the continuous elastic film during or just prior to a transition of the feed rate from the first feed rate to the second feed rate and such that the first and second cutting elements rotate through a non-cutting range while the feed rate is at the second feed rate.

17. The apparatus of claim 12, wherein the stretch unit further comprises:

a third pair of arms configured to pick-up another first film portion of the series of discrete first film portions from the vacuum drum, the third pair of arms being separable in the CD machine; and a fourth pair of arms configured to pick-up another second film portion of the series of discrete second film portions from the vacuum drum, the fourth pair of arms being separable in the CD machine;

wherein each of the third pair of arms and the fourth pair of arms separate outwardly in the CD direction as they move from the pickup position to the transfer position, such that the another first film portion and the another second film portion, respectively, are stretched in the CD direction.

18. The apparatus of claim 17, wherein the first pair of arms and the second pair of arms are positioned proximate each other and the third pair of arms and the fourth pair of arms are positioned proximate each other, with the third pair of arms and the fourth pair of arms positioned on an opposite side of the stretch unit from the first pair of arms and the second pair of arms.

19. A method of applying discrete stretched film portions to a carrier web, the method comprising:

operating a drive roll to feed a continuous elastic film in a machine direction (MD) onto a vacuum drum;

operating a cutting unit to form a series of discrete first film portions and discrete second film portions from the continuous elastic film; and operating a stretch unit comprising a plurality of pairs of arms to:

rotatably transfer the series of discrete first film portions and discrete second film portions from a pickup position off the vacuum drum to a transfer position onto the carrier web, with each pair of arms of the plurality of pairs of arms securing a respective first film portion or second film portion thereto;

between the pickup position and the transfer position, stretch each respective first film portion and second film portion in a cross-machine direction (CD) by separating each pair of arms of the plurality of pairs of arms in the CD; and deposit the series of discrete first film portions and discrete second film portions onto the carrier web at the transfer position;

wherein a first film portion and a second film portion of a first film portion pair deposited on the carrier web are separated in the MD by a first distance; and wherein a second film portion pair, including an another first film portion and an another second film portion, deposited on the carrier web is separated in the MD from the first film portion pair by a second distance greater than the first distance.

20. The method of claim 19, further comprising:

operating the drive roll to feed the continuous elastic film onto the vacuum drum at the first feed rate;

cutting the continuous elastic film with the cutting unit while the continuous elastic film is being fed at the first feed rate to form the first film portion pair;

subsequent to forming the first film portion pair, operating the drive roll to feed the continuous elastic film onto the vacuum drum at a second feed rate that is lower than the first feed rate;

operating the drive roll to again feed the continuous elastic film onto the vacuum drum at the first feed rate; and cutting the continuous elastic film with the cutting unit while the continuous elastic film is being fed at the first feed rate to form the second film portion pair.

21. The method of claim 19, further comprising:

operating a first pair of arms and a second pair of arms from the plurality of pairs of arms to rotatably transfer and stretch the first film portion and the second film portion of the first film portion pair; and operating a third pair of arms and a fourth pair of arms from the plurality of pairs of arms to rotatably transfer and stretch the another first film portion and the another second film portion of the second film portion pair.

22. An apparatus for applying stretched elastic segments to a carrier web, the apparatus comprising:

a drive roll configured to feed a continuous elastic film in a machine direction (MD);

a vacuum drum positioned to receive the continuous elastic film from the drive roll;

a cutting unit positioned adjacent the vacuum drum and configured to cut the continuous elastic film to create a series of discrete first film portions and discrete second film portions;

a rotating actuator configured to selectively drive the drive roll to feed the continuous elastic film onto the vacuum drum at one of a first feed rate and a second feed rate; and a controller operably connected to the rotating actuator; and a stretch unit to transfer the series of discrete first film portions and discrete second film portions from a pickup position off the vacuum drum to a transfer position onto the carrier web, the stretch unit comprising:

a first pair of arms configured to transfer a first film portion of the series of discrete first film portions from the vacuum drum, the first pair of arms being separable in a cross-machine direction (CD); and a second pair of arms configured to transfer a second film portion of the series of discrete second film portions from the vacuum drum, the second pair of arms being separable in the CD;

wherein each of the first pair of arms and the second pair of arms separate outwardly in the CD as they move from the pickup position to the transfer position, to stretch the first film portion and the second film portion, respectively, in the CD; and wherein the drive roll is operable to variably feed the continuous elastic film onto the vacuum drum at a first feed rate and a second feed rate that is slower than the first feed rate, wherein the controller is configured to coordinate operation of the cutting unit with operation of the rotating actuator, such that the cutting unit is configured to cut the continuous elastic film during or just prior to a transition of the feed rate from the first feed rate to the second feed rate and such that the rotating cutting wheel rotates through a non-cutting range while the feed rate is at the second feed rate.

* * * * *